United States Patent
Melnyk et al.

(10) Patent No.: US 9,714,245 B2
(45) Date of Patent: Jul. 25, 2017

(54) CARBOLINE COMPOUNDS USABLE IN THE TREATMENT OF NEURODEGENERATIVE DISEASES

(71) Applicants: ALZPROTECT, Loos (FR); UNIVERSITE DE LILLE 2 DROIT ET SANTE, Lille (FR); INSERM (Institut National de la Sante et de la Recherche Medicale), Paris (FR)

(72) Inventors: Patricia Melnyk, Annouellin (FR); Pascal Carato, Ronchin (FR); Stephane Burlet, Croix (FR); Emilie Nguyen, Le Mans (FR); Philippe Verwaerde, Santes (FR); Nicolas Sergeant, Ronchin (FR); Cecilia Estrella, Lomme (FR)

(73) Assignees: ALZPROTECT, Loos (FR); UNIVERSITE DE LILLE 2 DROIT ET SANTE, Lille (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 14/900,248

(22) PCT Filed: Jun. 27, 2014

(86) PCT No.: PCT/EP2014/063771
§ 371 (c)(1),
(2) Date: Dec. 21, 2015

(87) PCT Pub. No.: WO2014/207240
PCT Pub. Date: Dec. 31, 2014

(65) Prior Publication Data
US 2016/0152610 A1    Jun. 2, 2016

(30) Foreign Application Priority Data

Jun. 28, 2013  (EP) .................................... 13305927
Jun. 28, 2013  (EP) .................................... 13305928

(51) Int. Cl.
*C07D 471/04*  (2006.01)
*A61K 31/496*  (2006.01)

(52) U.S. Cl.
CPC .................. *C07D 471/04* (2013.01)

(58) Field of Classification Search
None
See application file for complete search history.

(56) References Cited

U.S. PATENT DOCUMENTS 4,663,456 A    5/1987  Abou-Gharbia

FOREIGN PATENT DOCUMENTS

| WO | 2006/051489 A1 | 11/2005 |
| WO | 2009/003003 A2 | 12/2008 |
| WO | 2013/062344 A1 | 5/2013 |

OTHER PUBLICATIONS

Rittman et al. ACHR, vol. 11(6), pp. 8-10 (2012).*
Ludolph et al. Eur. J.Neurol. 16(3) pp. 297-309 (2009).*
Hong-Qi et al. Translational Neurodegenration, pp. 1-12 (2012).*
Zhang et al. Molecular Brain 2011, 4:3, pp. 1-13.*
O'Brien et al. Annu Rev Neurosci. 2011 ; 34: 185-204.*
MacLeod et al. Future Sci. OA (2015) 1(3), pp. 1-16 downloaded at www.future-science.future science group com.*
Abisambra, Jose F. et al., "Tau accumulation activates the unfolded protein response by impairing endoplasmic reticulum-associated degradation" The Journal of Neuroscience (2013), vol. 33(22), pp. 9498-9507.
Aksanova, L.A. et al., "Preparation and pharmacological examination of a number of derivatives of tetrahydrobenzofuropyridine" Pharmaceutical Chemistry Journal (1975), vol. 9(1), pp. 5-7.
Database Registry Chemical Abstracts service, Columbus Feb. 22, 1986.
Nixon, Ralph A. et al., "Neurodegenerative lysosomal disorders" Autophagy (2008), vol. 4(5), pp. 590-599.
Dolan, Philip J. et al., "Decreases in valosin-containing protein result in increased levels of tau phosphorylated at ser26/356" FEBS Letters (2011), vol. 585, pp. 3424-3429.
Bartolome, Fernando et al., "Pathogenic VCP mutations induce mitochondrial uncoupling and reduced ATP levels" Neuron (2013), vol. 78, pp. 57-64.
The International Search Report (ISR) with Written Opinion for PCT/EP2014/063771 dated Aug. 4, 2014, p. 1-8.

* cited by examiner

*Primary Examiner* — Emily Bernhardt
(74) *Attorney, Agent, or Firm* — McDonnell Boehnen Hulbert & Berghoff

(57) ABSTRACT

The present invention relates to a compound according to Formula (A) or a pharmaceutically acceptable salt, solvate, clathrate, hydrate or polymorph thereof, and its use.

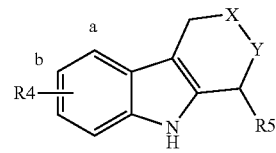

(A)

12 Claims, No Drawings

CARBOLINE COMPOUNDS USABLE IN THE TREATMENT OF NEURODEGENERATIVE DISEASES

This application is a U.S. national phase of International Application No. PCT/EP2014/063771, filed Jun. 27, 2014 which claims priority from European Patent Application No. 13305927.9 filed Jun. 28, 2013 and European Patent Application No. 13305928.7, filed Jun. 28, 2013, the disclosure of each of which is hereby incorporated by reference in its entirety.

TECHNICAL FIELD

The present invention relates to new compounds and the use thereof for the treatment of a disease related to a dysfunction of the Amyloid Precursor Protein (APP) and/or of a disease related to a modification of tau protein. An example of such disease is Alzheimer's disease (AD).

BACKGROUND OF THE INVENTION

AD is a progressive neurodegenerative disorder that gradually damages the neurons in regions of the brain involved in memory, learning and reasoning.

The diagnostic of AD is currently post mortem and consists in checking the presence of extracellular accumulation of amyloid β (Aβ) peptides forming amyloid deposits in the brain parenchyma. AD is currently incurable. AD is a multifactorial disease. The cause for most Alzheimer's cases is still essentially unknown (except for 1% to 5% of cases where genetic mutations have been identified).

Several competing hypotheses exist trying to explain the cause of AD.

On the one hand it has been proposed that amyloid beta (Aβ) deposits are the fundamental cause of the disease. Support for this postulate comes from the location of the Alzheimer genetic mutations located on APP gene, for the APP on Chromosome 21, together with the fact that people with trisomy 21 (Down Syndrome), who have an extra copy of the APP gene, almost universally exhibit AD by 40 years of age. APOE4, the major genetic risk factor for AD, also leads to excess amyloid buildup in the brain before AD symptoms arise. Thus, the amyloid cascade hypothesis places the amyloid production, oligomerization, aggregation and synaptoxicity at the center of Alzheimer etiopathogenesis. Further evidence comes from the finding that transgenic mice, which express a mutant form of the human APP gene, develop fibrillar amyloid deposits and Alzheimer's-like brain pathology with spatial learning deficits.

On the other hand, AD is also known as a tauopathy. In tauopathies, abnormally and hyperphosphorylated tau protein isoforms aggregate into fibrillar structures within neurons to form the so-called neurofibrillary tangles (NFTs). The precise mechanism of tangle formation is not completely understood but mutations of tau gene—also called MAPT for microtubule-associated protein tau—are associated with the development of a tauopathy named Frontotemporal Dementia with Parkinsonism linked to chromosome 17.

Neurodegeneration results in the progressive loss of structure or function of neurons, leading to their death. Many neurodegenerative diseases, including Parkinson's (PD), Alzheimer's, Huntington's (HD) diseases, amyotrophic lateral sclerosis (ALS) with frontotemporal dementia, inclusion body myopathy with Paget's bone disease and frontotemporal dementia (IBMPFD) occur as a result of neurodegenerative processes. As research progresses, many similarities appear relating these diseases to each other in terms of common physiopathological hallmarks from the subcellular level to the clinical symptoms observed in patients. Noteworthy, the whole spectrum of these neurodegenerative diseases are associated to the accumulation and aggregation of unfolded or mis-folded proteins such as synuclein, amyloid peptide, microtubule-associated protein tau, huntingtin, TDP-43, FUS/TLS etc.

The degradation of altered or pathologically mis-folded proteins is a complex phenomenon, which takes many cellular paths and is likely deregulated in a large number of pathologies. At the crossroads of cellular systems of protein degradation such as endosome/lysosome, endoplasmic reticulum associated-degradation, autophagy and ubiquitin-proteasome system, VCP (Valosin Containing Protein), also referred as p97 or CDC48, is a new therapeutic target for the treatment of neurodegenerative diseases and cancers. VCP is a member of AAA+/ATPase enzyme family (ATPases are associated with various cellular activities) and is involved in a growing number of cellular mechanims: cellular division, organelle biogenesis, nucleus membrane formation, DNA repair, transport and vesicules fusion, protein degradation and suppression of protein aggregates. It is associated with cofactors such as with HSP90, Ufd1 or Np14. Its importance has been demonstrated in several diseases. In particular, mutations in VCP/p97 gene have been shown to be linked to IBMPFD and some familial ALS. Moreover, several neurodegenerative diseases are associated to protein degradation dysfunction (Nixon R A, Yang D S, Lee J Y. Autophagy, 2008, 4, 590-99). The possible linkage of VCP to the AD-relevant protein Tau was recently proposed (Dolan P J, Jin Y N, Hwang W, Johnson G V. FEBS Lett, 2011, 585, 3424-9; Abisambra JF1, Jinwal U K, Blair L J, O'Leary J C 3rd, Li Q, Brady S, Wang L, Guidi C E, Zhang B, Nordhues B A, Cockman M, Suntharalingham A, Li P, Jin Y, Atkins C A, Dickey C A. J Neurosci. Tau accumulation activates the unfolded protein response by impairing endoplasmic reticulum-associated degradation. 2013 May 29; 33(22):9498-507. doi: 10.1523/JNEUROSCI.5397-12.2013). VCP/p97, which is essential for the maturation of ubiquitin containing autophagosomes, is a potential therapeutic target of choice for the treatment of neurodegenerative diseases.

Document WO 2006/051489 describes the use of 1,4-bis (3-aminoalkyl)piperazine derivatives in the treatment of neurodegenerative diseases, particularly in the treatment of AD. The compounds disclosed in the afore-mentioned document are able to a) increase the carboxy-terminal fragments of APP (APP-CTFs) which all in common possess the last 50 amino acids of APP, and especially those having potential physiological activities, such as the α-stubs (APP-CTF alpha) and the ε-stubs (APP-CTF gamma or AICD for APP intra cellular domain), b) increase the soluble fragment sAPPα, c) decrease the production of neurotoxic by-products of APP, i.e. β-amyloid (Aβ) peptides, especially in their form x-42 and d) without modifying the APP expression and in the absence of neurotoxicity.

An object of the present invention is to provide new compounds that can be useful as drugs, especially for the treatment of diseases related with APP disorder, for the treatment of tauopathies and more particularly for the treatment of neurodegenerative diseases such as AD, Lewy body disease, Down syndrome, amyloid angiopathy, PD, ALS, frontotemporal lobar degeneration and IBMPFD.

Another object of the present invention is to provide compounds having an effect on Tau pathology.

Another object of the present invention is to provide compounds having a biological activity in at least one of the afore-mentioned mechanisms a) to d) as regard to β-amyloid (Aβ) peptides and the afore-mentioned mechanisms as regards tau pathology.

Another object is to provide compounds useful as drugs, especially for the treatment of the afore-mentioned diseases, said compounds having an improved efficiency and/or an improved solubility and/or an improved toxicity and/or an improved in vivo stability and/or an improved biodisponibility and/or said compounds being easier to synthesize at an industrial scale.

Another object of the present invention is to provide compounds that can be active, when orally administered.

Another object of the invention is to provide compounds able to interact and/or react with VCP/p97.

Another object of the present invention is to provide a pharmaceutical composition comprising the compounds of the present invention. Advantageously, this composition can be orally administered.

SUMMARY OF THE INVENTION

Accordingly, the present invention provides a compound according to Formula (A)

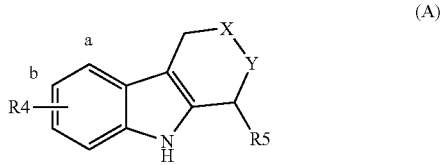

(A)

or a pharmaceutically acceptable salt, solvate, clathrate, hydrate or polymorph thereof, wherein
X and Y are different from one another and are selected from:

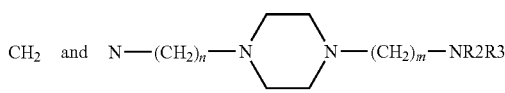

wherein
n is an integer equal to 2 or superior to 2;
m is an integer equal to 2 or superior to 2; and
R2 and R3 are selected independently from one another from the groups consisting of:
linear or branched ($C_1$-$C_{12}$) alkyl; linear or branched ($C_2$-$C_{12}$) alkenyl; linear or branched ($C_2$-$C_{12}$) alkynyl; said alkyl group, alkenyl group or alkynyl group may be substituted with at least one substituent selected from halogen, cycloalkyl, hydroxyl, alkoxy, amino, acylamino, aroylamino, heteroaroylamino and carboxy groups;

heteroaroylamino;
($C_2$-$C_6$) heterocycloalkyl comprising in the cycle an oxygen atom and/or a nitrogen atom;
benzyl optionally substituted with an alkyl group, halogen, an ether group and/or an amino group; or
R2 and R3 form together with the nitrogen atom carrying them a saturated or unsaturated ($C_2$-$C_7$) heterocycle;
R4 is selected from F, Cl, H, O—$CH_3$, and —$CH_3$;
R5 is selected from H, $CH_3$ and a phenyl group;
with the proviso that R5 is H if X is not $CH_2$.

The compounds according to the invention are able to increase APP-CTF alpha and AICD, as previously mentioned. They can be therapeutically efficient without involving cell toxicity.

The compounds of the invention can be easily synthesized and at low cost.

The compounds according to the invention are also active on VCP/p97 and thus are multi-target drugs.

DETAILED DESCRIPTION OF THE INVENTION

As noted above, the invention relates to compounds of Formula (A), as well as their pharmaceutically acceptable salts, solvates, clathrates, hydrates, and polymorphs.

According to the invention, m and n may be identical or different from one another, m and n can be equal to 2 or to any integer superior to 2. Advantageously, m and n are independently selected from 2 and 3. Advantageously, m and n are identical and e.g. equal to 2 or 3.

According to one embodiment, R2 and R3 are identical and are selected from ($C_1$-$C_{12}$) alkyls.

Accordingly, R2 and R3 may be identical and either isobutyl or methyl groups. These compounds are particularly in vitro active.

Advantageously, R4 is selected from F, Cl, H and O—$CH_3$ and advantageously, R4 is F.

R4 may be attached to the carbon atom in position b.

According to the invention, R2, R3 and the nitrogen atom carrying them may form one of the following heterocyclic groups:

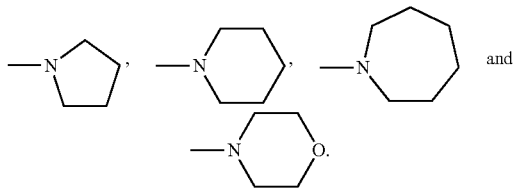

Accordingly, R2, R3 and the nitrogen atom carrying them may form a pyrrolidinyl group.

Particularly preferred compounds of the invention are those selected from the group consisting of:

| Compound no. | Structure | Name |
|---|---|---|
| 3.1a | 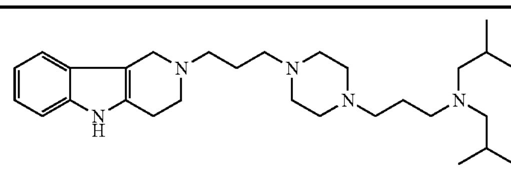 | N,N-diisobutyl-3-[4-(3-(1,3,4,5-tetrahydro-1H-pyrido[4,3-b]indol-2-yl)propyl)piperazin-1-yl]propylamine |

| Compound no. | Structure | Name |
|---|---|---|
| 3.1b | 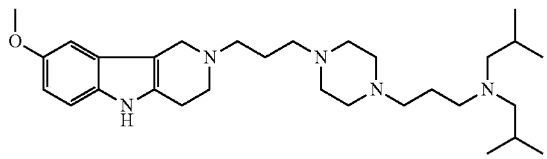 [SMILES: COc1ccc2[nH]c3c(c2c1)CN(CCCN1CCN(CCCN(CC(C)C)CC(C)C)CC1)CC3] | N,N-diisobutyl-3-(4-(3-(8-methoxy-1,3,4,5-tetrahydro-1H-pyrido[4,3-b]indol-2-yl)propyl)piperazin-1-yl)propylamine |
| 3.1c | 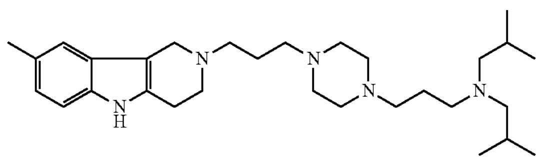 [SMILES: Cc1ccc2[nH]c3c(c2c1)CN(CCCN1CCN(CCCN(CC(C)C)CC(C)C)CC1)CC3] | N,N-diisobutyl-3-[4-(3-(8-methyl-1,3,4,5-tetrahydro-1H-pyrido[4,3-b]indol-2-yl)propyl)piperazin-1-yl]propylamine |
| 3.1d | 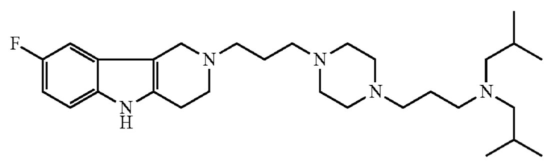 [SMILES: CC(C)CN(CCCN1CCN(CCCN2CCc3[nH]c4ccc(F)cc4c3C2)CC1)CC(C)C] | N,N-diisobutyl-3-(4-(3-(8-fluoro-1,3,4,5-tetrahydro-1H-pyrido[4,3-b]indol-2-yl)propyl)piperazin-1-yl)propylamine |
| 3.1f | 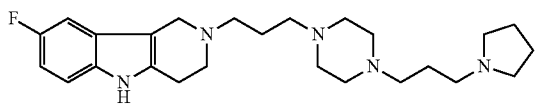 [SMILES: Fc1ccc2[nH]c3c(c2c1)CN(CCCN1CCN(CCCN2CCCC2)CC1)CC3] | 8-Fluoro-2-{3-[4-(3-(pyrrolidin-1-yl)propyl)piperazin-1-yl]propyl}-2,3,4,5-tetrahydro-1H-pyrido[4,3-b]indole |
| 3.1g | 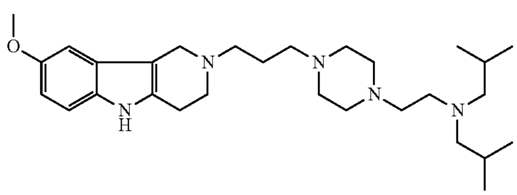 [SMILES: COc1ccc2[nH]c3c(c2c1)CN(CCCN1CCN(CCN(CC(C)C)CC(C)C)CC1)CC3] | N,N-diisobutyl-2-(4-(3-(8-methoxy-1,3,4,5-tetrahydro-1H-pyrido[4,3-b]indol-2-yl)propyl)piperazin-1-yl)ethylamine |
| 3.1h | 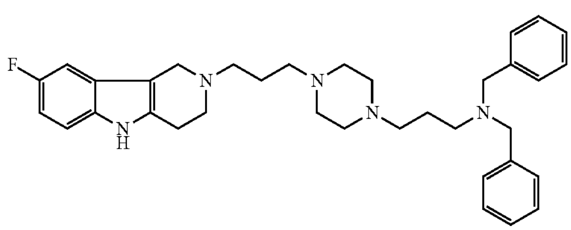 [SMILES: Fc1ccc2[nH]c3c(c2c1)CN(CCCN1CCN(CCCN(Cc2ccccc2)Cc2ccccc2)CC1)CC3] | N,N-dibenzyl-3-[4-(3-(8-fluoro-1,3,4,5-tetrahydro-1H-pyrido[4,3-b]indol-2-yl)propyl)piperazin-1-yl]propylamine |
| 3.1i | 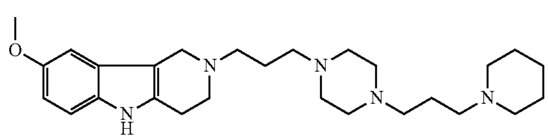 [SMILES: COc1ccc2[nH]c3c(c2c1)CN(CCCN1CCN(CCCN2CCCCC2)CC1)CC3] | 3-(4-(3-(8-methoxy-1,3,4,5-tetrahydro-1H-pyrido[4,3-b]indol-2-yl)propyl)piperazin-1-yl)propylpiperidine |
| 3.2a | 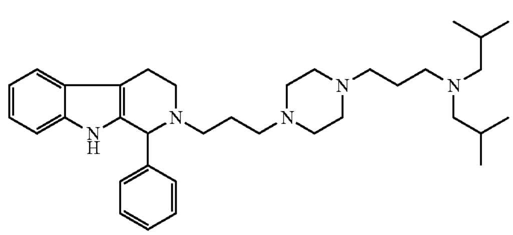 [SMILES: CC(C)CN(CCCN1CCN(CCCN2CCc3c([nH]c4ccccc34)C2c2ccccc2)CC1)CC(C)C] | N,N-diisobutyl-3-{4-[3-(1-phenyl-1,3,4,9-tetrahydro-1H-beta-carbolin-2-yl)propyl]piperazin-1-yl}propylamine |

| Compound no. | Structure | Name |
|---|---|---|
| 3.2b | 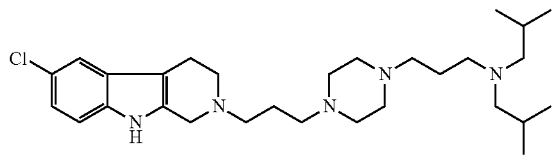 [SMILES: CC(C)CN(CCCN1CCN(CCCN2CCc3c([nH]c4ccc(Cl)cc34)C2)CC1)CC(C)C] | N,N(diisobutyl-3-{4-[3-(6-chloro-1,3,4,9-tetrahydro-1H-beta-carbolin-2-yl)propyl]piperazin-1-yl}propylamine |
| 3.2d | 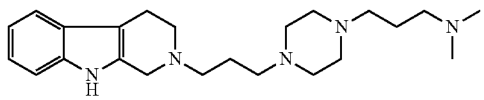 [SMILES: CN(C)CCCN1CCN(CCCN2CCc3c([nH]c4ccccc34)C2)CC1] | N,N-dimethyl-3-(4-(3-(1,3,4,9-tetrahydro-1H-beta-carbolin-2-yl)propyl)piperazin-1-yl)propylamine |
| 3.2e | 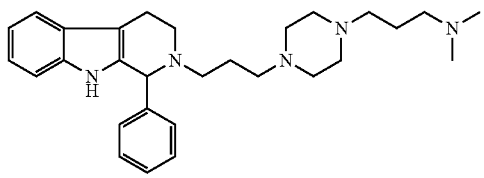 [SMILES: CN(C)CCCN1CCN(CCCN2CCc3c([nH]c4ccccc34)C2c2ccccc2)CC1] | N,N-dimethyl-3-(4-(3-(1-phenyl-1,3,4,9-tetrahydro-1H-beta-carbolin-2-yl)propyl)piperazin-1-yl)propylamine |
| 3.2h | 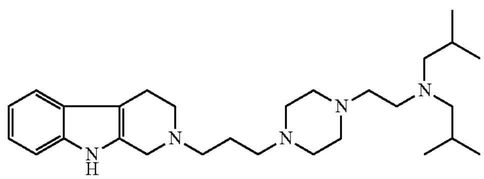 [SMILES: CC(C)CN(CCN1CCN(CCCN2CCc3c([nH]c4ccccc34)C2)CC1)CC(C)C] | N,N-diisobutyl-2-{4-[3-(1,3,4,9-tetrahydro-1H-beta-carbolin-2-yl)propyl]piperazin-1-yl}ethylamine |
| 3.2i | 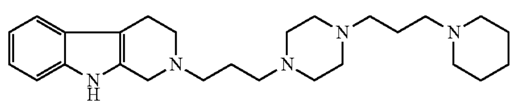 [SMILES: c1ccc2c3c([nH]c2c1)CN(CCCN1CCN(CCCN2CCCCC2)CC1)CC3] | 1-[3-(piperidin-1-yl)propyl]-4-(3-{1H,2H,3H,4H,9H-pyrido[3,4-b]indol-2-yl}propyl)piperazine |
| 3.2j | 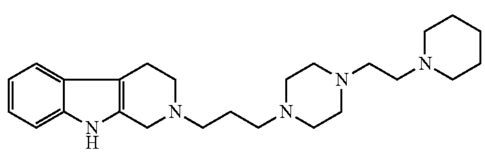 [SMILES: c1ccc2c3c([nH]c2c1)CN(CCCN1CCN(CCN2CCCCC2)CC1)CC3] | 1-[2-(piperidin-1-yl)ethyl]-4-(3-{1H,2H,3H,4H,9H-pyrido[3,4-b]indol-2-yl}propyl)piperazine |
| 3.2k | 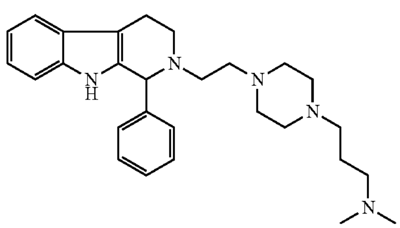 [SMILES: CN(C)CCCN1CCN(CCN2CCc3c([nH]c4ccccc34)C2c2ccccc2)CC1] | N,N-dimethyl-3-(4-(2-(1-phenyl-1,3,4,9-tetrahydro-1H-beta-carbolin-2-yl)ethyl)piperazin-1-yl)propylamine |

In a first embodiment, the compound of the invention is a compound according to Formula (I)

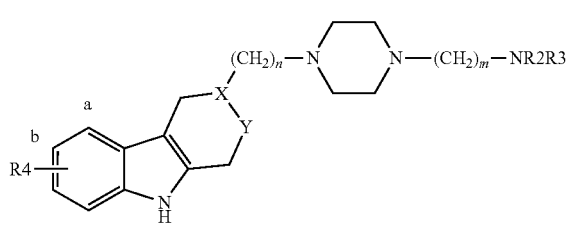

in which
n is an integer equal to 2 or superior to 2;
R4 is selected from F, Cl, H, O—CH$_3$, and —CH$_3$;
m is an integer equal to 2 or superior to 2;
R2 and R3 are selected independently from one another from the groups consisting of:
linear or branched ($C_1$-$C_{12}$) alkyl; linear or branched ($C_2$-$C_{12}$) alkenyl; linear or branched ($C_2$-$C_{12}$) alkynyl; said alkyl group, alkenyl group or alkynyl group may be substituted with at least one substituent selected from halogen, cycloalkyl, hydroxyl, alkoxy, amino, acylamino, aroylamino, heteroaroylamino and carboxy groups;
heteroaroylamino;
($C_2$-$C_6$) heterocycloalkyl comprising in the cycle an oxygen atom and/or a nitrogen atom;
benzyl optionally substituted with an alkyl group, halogen, an ether group and/or an amino group; or R2 and R3 form together with the nitrogen atom carrying them a saturated or unsaturated ($C_2$-$C_7$) heterocycle;

or a pharmaceutically acceptable salt, solvate, clathrate, hydrate or polymorph thereof.

In this second embodiment, m and n may be identical or different from one another, m and n can be equal to 2 or to any integer superior to 2. Advantageously, m and n are independently selected from 2 and 3. Advantageously, m and n are identical and for example both equal to 2 or 3.

According to one aspect of this first embodiment, R2 and R3 are identical and are selected from ($C_1$-$C_{12}$) alkyls.

R2 and R3 may be identical and either isobutyl or methyl groups. These compounds are particularly in vitro active.

R4 may be attached to the carbon atom in position b. In that case, it may also be selected from F, Cl, H and O—$CH_3$. Preferably R4 is selected from H and F. More preferably, R4 is F. Such compounds are more active on AICD.

According to another aspect of this first embodiment, R2, R3 and the nitrogen atom carrying them may form one of the following heterocyclic groups:

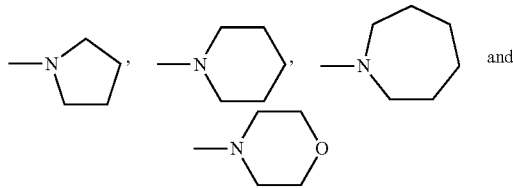

Accordingly, R2, R3 and the nitrogen atom carrying them may form a pyrrolidinyl group. These compounds are particularly in vivo stable.

Preferred compounds of this first embodiment are those selected from the group consisting of:

N,N-diisobutyl-3-[4-(3-(1,3,4,5-tetrahydro-1H-pyrido[4,3-b]indol-2-yl)propyl)piperazin-1-yl]propylamine (compound 3.1a), N,N-diisobutyl-3-(4-(3-(8-methoxy-1,3,4,5-tetrahydro-1H-pyrido[4,3-b]indol-2-yl)propyl)piperazin-1-yl)propylamine (compound 3.1b), N,N-diisobutyl-3-[4-(3-(8-methyl-1,3,4,5-tetrahydro-1H-pyrido[4,3-b]indol-2-yl)propyl)piperazin-1-yl]propylamine (compound 3.1c), N,N-diisobutyl-3-(4-(3-(8-fluoro-1,3,4,5-tetrahydro-1H-pyrido[4,3-b]indol-2-yl)propyl)piperazin-1-yl)propylamine (compound 3.1d), 8-Fluoro-2-{3-[4-(3-(pyrrolidin-1-yl)propyl)piperazin-1-yl]propyl}-2,3,4,5-tetrahydro-1H-pyrido[4,3-b]indole (compound 3.1f), N,N-diisobutyl-2-(4-(3-(8-methoxy-1,3,4,5-tetrahydro-1H-pyrido[4,3-b]indol-2-yl)propyl)piperazin-1-yl)ethylamine (compound 3.1g), N,N-dibenzyl-3-[4-(3-(8-fluoro-1,3,4,5-tetrahydro-1H-pyrido[4,3-b]indol-2-yl)propyl)piperazin-1-yl]propylamine (compound 3.1h), 3-(4-(3-(8-methoxy-1,3,4,5-tetrahydro-1H-pyrido[4,3-b]indol-2-yl)propyl)piperazin-1-yl)propylpiperidine (compound 3.1i).

In a second embodiment, the compound of the invention is a compound according to Formula (II)

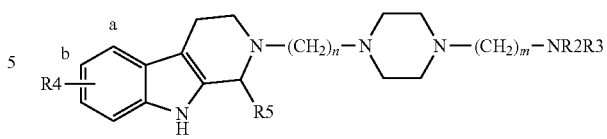

in which:

n is an integer equal to 2 or superior to 2;

R4 is selected from F, Cl, H, O—$CH_3$, and —$CH_3$;

R5 is selected from H, $CH_3$ and a phenyl group;

m is an integer equal to 2 or superior to 2;

R2 and R3 are selected independently from one another from the groups consisting of:

linear or branched ($C_1$-$C_{12}$) alkyl, linear or branched ($C_2$-$C_{12}$) alkenyl; linear or branched ($C_2$-$C_{12}$) alkynyl; said alkyl group, alkenyl group or alkynyl group may be substituted with at least one substituent selected from halogen, cycloalkyl, hydroxyl, alkoxy, amino, acylamino, aroylamino, heteroaroylamino and carboxy groups;

heteroaroylamino;

($C_2$-$C_6$) heterocycloalkyl comprising in the cycle an oxygen atom and/or a nitrogen atom;

benzyl optionally substituted with an alkyl group, halogen, an ether group and/or an amino group; or R2 and R3 form together with the nitrogen atom carrying them a saturated or unsaturated ($C_2$-$C_7$) heterocycle;

or a pharmaceutically acceptable salt, solvate, clathrate, hydrate or polymorph thereof.

In this second embodiment, m and n may be identical or different from one another, m and n can be equal to 2 or to any integer superior to 2. Advantageously, m and n are independently selected from 2 and 3. Advantageously, m and n are identical and equal to 2 or 3. Advantageously, m=n=3.

Advantageously, R5 is H or a phenyl group. When R5 is a phenyl group, the compounds of the invention are more efficient on AICD.

According to one aspect of this second embodiment, R2 and R3 are identical and are selected from ($C_1$-$C_{12}$) alkyls.

Accordingly, R2 and R3 may be identical and either isobutyl or methyl groups. These compounds are particularly in vitro active. Advantageously, R2 and R3 are methyl groups.

Advantageously, R4 is selected from F, Cl, H and O—$CH_3$ and advantageously, R4 is F.

R4 may be attached to the carbon atom in position b.

According to another aspect of this second embodiment, R2, R3 and the nitrogen atom carrying them may form one of the following heterocyclic groups:

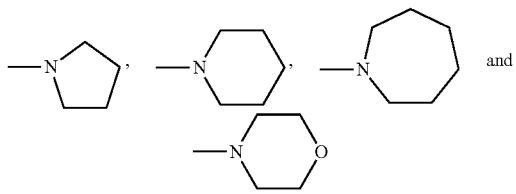

Accordingly, R2, R3 and the nitrogen atom carrying them may form a pyrrolidinyl group.

Preferred compounds of this second embodiment are those selected from the group consisting of:

N,N-diisobutyl-3-{4-[3-(1-phenyl-1,3,4,9-tetrahydro-1H-beta-carbolin-2-yl)propyl]piperazin-1-yl}propylamine (compound 3.2a), N,N-diisobutyl-3-{4-[3-(6-chloro-1,3,4,9-tetrahydro-1H-beta-carbolin-2-yl)propyl]piperazin-1-yl}propylamine (compound 3.2b), N,N-dimethyl-3-(4-(3-(1,3,4,9-tetrahydro-1H-beta-carbolin-2-yl)propyl)piperazin-1-yl)propylamine (compound 3.2d), N,N-dimethyl-3-(4-(3-(1-phenyl-1,3,4,9-tetrahydro-1H-beta-carbolin-2-yl)propyl)piperazin-1-yl)propylamine (compound 3.2e), N,N-diisobutyl-3-{4-[3-(1,3,4,9-tetrahydro-1H-beta-carbolin-2-yl)propyl]piperazin-1-yl}ethylamine (compound 3.2h), 1-[3-(piperidin-1-yl)propyl]-4-(3-{1H,2H,3H,4H,9H-pyrido[3,4-b]indol-2-yl}propyl)piperazine (compound 3.2i), 1-[2-(piperidin-1-yl)ethyl]-4-(3-{1H,2H,3H,4H,9H-pyrido[3,4-b]indol-2-yl}propyl)piperazine (compound 3.2j), N,N-dimethyl-3-(4-(2-(1-phenyl-1,3,4,9-tetrahydro-1H-beta-carbolin-2-yl)ethyl)piperazin-1-yl)propylamine (compound 3.2k).

The present invention also relates to the compounds of Formula (A) and subformulae for their use as a medicament, especially for their use as a medicament in the treatment of a disease selected from the group consisting of tauopathies, amyloidopathies and synucleopathies and more particularly neurodegenerative diseases, related neurodegenerative diseases, developmental diseases or cancer and, for example, Alzheimer's disease, Paget's disease of bone, fronto temporal lobar dementia, familial amyotrophic lateral sclerosis, Lewy body disease, Down syndrome, amyloid angiopathy, Parkinson's disease, amyotrophic lateral sclerosis (ALS) and frontotemporal degeneration.

Paget's disease of bone, fronto temporal lobar dementia, familial amyotrophic lateral sclerosis and Alzheimer's disease are diseases already known as diseases linked with VCP/p97 modifications. In particular, these diseases are linked with modifications of VCP/p97 localisation or activity (Bartolome F1, Wu H C, Burchell V S, Preza E, Wray S, Mahoney C J, Fox N C, Calvo A, Canosa A, Moglia C, Mandrioli J, Chiò A, Orrell R W, Houlden H, Hardy J, Abramov A Y, Plun-Favreau H. Pathogenic VCP mutations induce mitochondrial uncoupling and reduced ATP levels. Neuron. 2013 Apr. 10; 78(1):57-64. doi: 10.1016/j.neuron.2013.02.028).

The present invention also relates to a pharmaceutical composition comprising as an active ingredient, a compound according to the invention and a pharmaceutically acceptable carrier, diluent, excipient and/or adjuvant. The pharmaceutical composition according to the invention may also comprise at least one other pharmaceutically active ingredient for the treatment of one of the above-mentioned diseases.

The pharmaceutical composition according to the invention may be in a dosage form suitable for oral administration (including sublingual administration), for parenteral administration (such as intravenous, intramuscular or subcutaneous injection or intravenous infusion), intracisternal or intraperitoneal administration for topical administration (including ocular, transdermal and mucosal administration such as intranasal administration), by a skin patch, an inhalator, an implant or a suppository. The composition according to the present invention may be liquid, like for example, a syrup. The composition of the invention may also be a powder which can be diluted with water, for example, prior to use. It may also be solid or semi-solid depending on the carrier, diluent, adjuvant and/or excipient used for the preparation of the composition according to the invention. The person skilled in the art is able to select carrier, diluent, adjuvant and/or excipient according to the most suitable method of administration. For example, the person skilled in the art may refer to the latest edition of Remington's Pharmaceutical Sciences.

Examples of dosage forms that can be used according to the invention include, but are not limited to, tablets, pills, powders, lozenges, sachets, cachets, elixirs, suspensions, emulsions, solutions, syrups, aerosols, ointments, creams, lotions, soft and hard gelatin capsules, suppositories, drops, sterile injectable solutions and sterile packaged powders that may be reconstituted before use, for administration as a bolus and/or for continuous administration. Carriers, excipients, diluents and/or adjuvants are selected according to the method of administration. They may be selected from lactose, dextrose, sucrose, sorbitol, mannitol, starches, gum acacia, calcium phosphate, alginates, gelatin, microcrystalline cellulose gelatin, calcium silicate, microcrystalline cellulose, polyvinylpyrrolidone, polyethylene glycol, cellulose, (sterile) water, methylcellulose, methyl and propylhydroxybenzoates, talc, magnesium stearate, edible oils, vegetable oils and mineral oils or suitable mixtures thereof. The pharmaceutical composition can optionally contain other substances which are commonly used in pharmaceutical formulations, such as lubricants, wetting agents, emulsifying and suspending agents, dispersing agents, disintegrating agents, stabilizing agents, isotonic agents, bulking agents, fillers, preserving agents, sweetening agents, flavoring agents, perfuming agents, coloring agents, antibacterial agents and/or antifungal agents such as parabens, chlorobutanol, phenol, sorbic acid, dispensing agents, flow regulators, release agents, etc. The composition may also be formulated so as to provide rapid, sustained or delayed release of the active compound(s) contained therein. For example, the composition according to the present invention may comprise nanoparticles carrying at least one compound of the invention. The compound according to the invention may be inside the nanoparticle or outside thereof, for example, linked to the surface thereof.

The pharmaceutical compositions of the invention may be in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. In general, such a unit dosage will contain from 1 mg to 600 mg of at least one compound of the invention. For example, a unit dosage may contain 2 mg, 50 mg, 100 mg or 200 mg of at least one compound according to the invention. For example one, two or three unit dosages may be administered per day, with about 6 hours between two administrations.

Depending on the use of the composition for prevention or treatment and depending on the route of administration, the active compound of the invention will usually be administered in a daily amount equal to 0.1 mg/Kg or superior to 0.1 mg/kg and inferior to 50 mg/kg or equal to 50 mg/kg, for example about 0.5, 1, 5, 10, 15, 20, 25, 30, 35, 40, 45 or 50 mg, per kilogram body weight of the patient, and it may be administered as a single daily dose.

DEFINITIONS

According to the present invention, the term "alkyl group" means a saturated aliphatic hydrocarbon group which may be straight (linear) or branched and having advantageously 1 to 12 carbon atoms in the chain. Preferably, when not specified, an alkyl group according to the invention may have 1 to 12, preferably 1 to 10, more preferably 1 to 6 carbon atoms and even more preferably 1, 2, 3 or 4 carbon atoms.

The term "alkenyl group" refers to an aliphatic hydrocarbon group which may be straight (linear) or branched and which comprises at least one double bond between two carbons. The alkenyl group may have advantageously 2 to 12 carbon atoms in the chain. Preferably, when not specified, an alkenyl group according to the invention may have 2 to 12, preferably 2 to 10, more preferably 2 to 6 carbon atoms and even more preferably 2, 3 or 4 carbon atoms. The alkenyl group may have only one double bond.

The term "alkynyl group" refers to an aliphatic hydrocarbon group which may be straight (linear) or branched and comprising at least one triple bond between two carbons. The alkynyl group may have advantageously 2 to 12 carbon atoms in the chain. Preferably, when not specified, an alkynyl group according to the invention may have 2 to 12, preferably 2 to 10, more preferably 2 to 6 carbon atoms and even more preferably 2, 3 or 4 carbon atoms. The alkynyl group may comprise only one triple bond.

The term "branched" means that one or more lower alkyl groups, alkenyl groups or alkynyl groups selected from methyl, ethyl, ethenyl, ethynyl, propyl, propenyl, propynyl and butyl, butenyl and butynyl are attached to one carbon of a linear alkyl, alkenyl or alkynyl chain. When at least two lower alkyl groups are attached to one carbon atom of the aforementioned linear chain, they may be attached on the same carbon atom or not. Advantageously, when the two (or more) lower alkyl, alkylenyl or alkynyl groups are attached to the same carbon atom of the linear alkyl chain, they may be attached to the free-end carbon atom of the linear chain, i.e. the carbon atom ending the molecule of the invention. According to the present invention, a "branched alkyl group" may be for example, isobutyl, isopentyl, isohexyl, isoheptyl, isooctyl, isononyl, isodecyl, isoundecanyl or isododecanyl group.

The alkyl, alkenyl and alkynyl group may be substituted with one or more "alkyl group substituent" which may be identical or different and include, for example, halogen, cycloalkyl, hydroxyl, alkoxy, amino, acylamino, aroylamino groups.

The term "halogen" refers to a halogen atom and advantageously represents F, Cl and Br atoms.

The term "cycloalkyl" refers to saturated and unsaturated cyclic, bicyclic, tricyclic and polycyclic hydrocarbon groups having preferably for each cyclic group 3 to 12 carbon atoms. Preferably, according to the present invention, the cycloalkyls are saturated cycles.

The term "alkoxy" refers to an R—O, wherein R is an alkyl group as previously defined, an alkyl group substituted by an alkyl group substituent as herein defined, an alkenyl group as herein defined or an alkenyl group substituted by an alkyl group substituent as herein defined.

The term "amino" refers to any group having the following formula RR'N— wherein R and R' are, independently from one another, selected from an hydrogen atom, an alkyl group as previously defined, an alkyl group substituted by an "alkyl group substituent" as herein defined, an alkenyl group as previously defined, an alkenyl group substituted by an "alkyl group substituent", an alkynyl group or an alkynyl group substituted by an "alkyl group substituent".

The term "acylamino" refers to any group having the formula RCON— wherein R is an alkyl group as previously defined, an alkyl group substituted by an "alkyl group substituent" as herein defined, an alkenyl group as previously defined, an alkenyl group substituted by an "alkyl group substituent", an alkynyl group or an alkynyl group substituted by an "alkyl group substituent".

The term "aroylamino" means a ϕCON, wherein ϕ is an aromatic group, such as for example, a phenyl group; ϕ may also be polycyclic.

The term "heteroaroylamino" refers to any group ϕ'CON—, wherein ϕ' is an aromatic group, optionally polycyclic, comprising in at least one cycle thereof an oxygen atom or a nitrogen atom or a sulfur atom as a heteroatom.

The term "carboxy groups" refers to any RCOO— group wherein R is an alkyl group as previously defined, an alkyl group substituted by an "alkyl group substituent" as herein defined, an alkenyl group as previously defined, an alkenyl group substituted by an "alkyl group substituent", an alkynyl group or an alkynyl group substituted by an "alkyl group substituent".

An "ether group" is, according to the present invention, a ROR' group wherein R and R' are different or identical and are selected from alkyl, alkenyl and alkynyl groups as previously defined, alkyl groups substituted by an "alkyl group substituent" as herein defined, alkenyl groups as previously defined and alkenyl groups substituted by an "alkyl group substituent". R and R' may form a cycle thereby forming a cyclic ether. According to the invention, R or R' is attached to one carbon of the benzyl group.

The term "pharmaceutically acceptable" means suitable for use in contact with the cells of a living organism, especially a mammal and more especially a human being, without undue toxicity, irritation, immune response or the like and providing a reasonable benefit/risk balance.

The term "pharmaceutically acceptable salt(s)" refers to any salt obtained from a compound of the invention, said salt having a slightly similar biological activity compared to the biological activity of said compound of the invention. Salts according to the present invention may be obtained from organic and inorganic acids or bases. Pharmaceutically acceptable salts are for example reviewed in "Berge, et al ((1997) J. pharm. Sd, vol 66, 1).

Suitable pharmaceutically acceptable salt may be selected from hydrochlorides, sulfates, bisulfates and/or phosphates.

The term "treatment" and derived terms mean reversing, alleviating, stopping or preventing the disorder and/or at least one symptom linked to said disorder. The term "treatment" also refers to a prophylactic treatment which can delay the onset of the above-mentioned diseases.

The compounds of the present invention may be used for the treatment of any living organism, more especially a mammal and more particularly a human and more particularly a human over 65 years old.

Experimental Part

Chemical Part

In the further mentioned general schemes, n, m, R2, R3, R4, and R5 refer to the values and groups as defined above, respectively.

Scheme 1: Preparation of intermediates chloroalkyl-piperazine derivatives

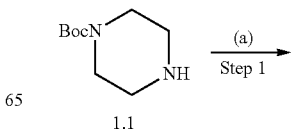

1.1

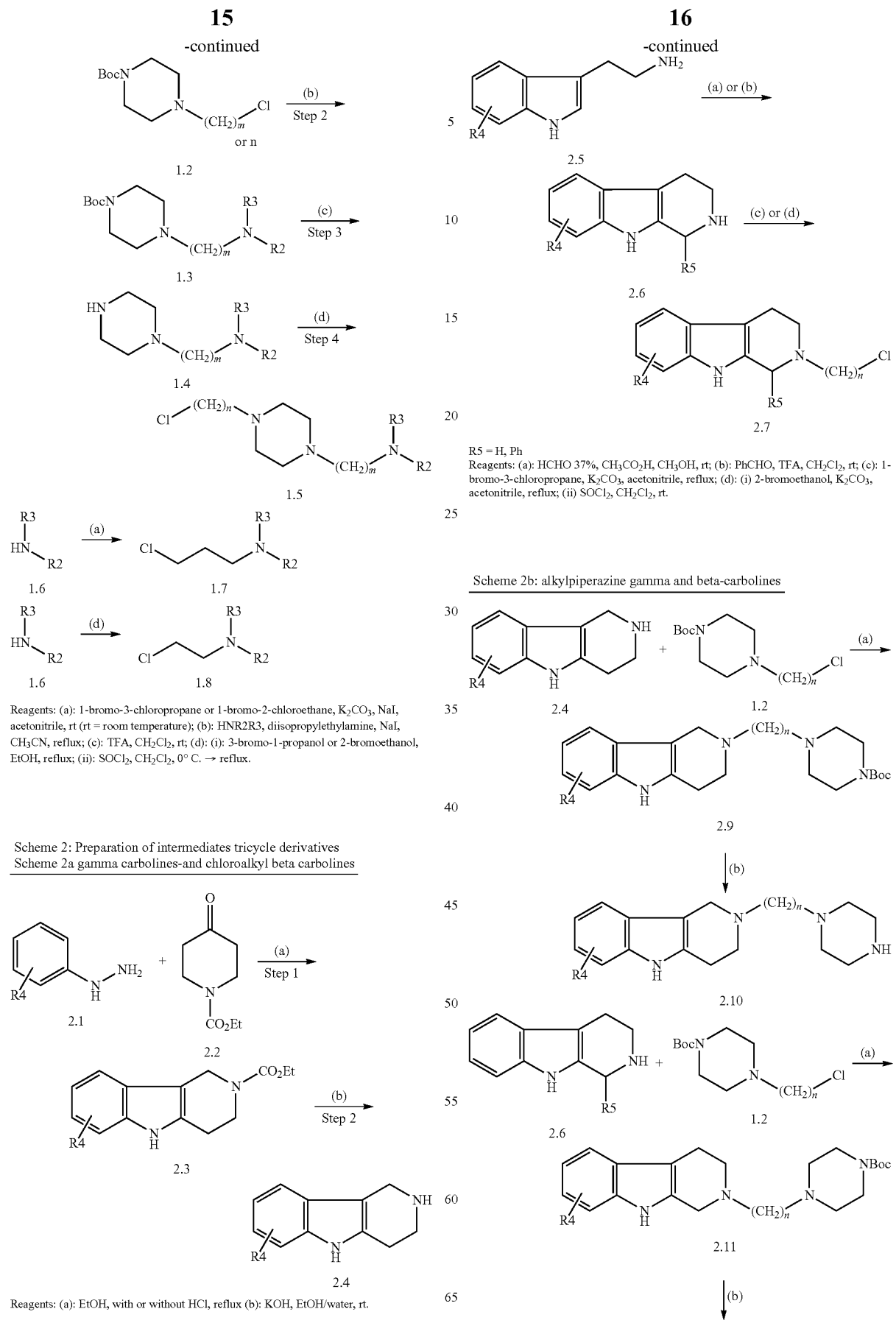

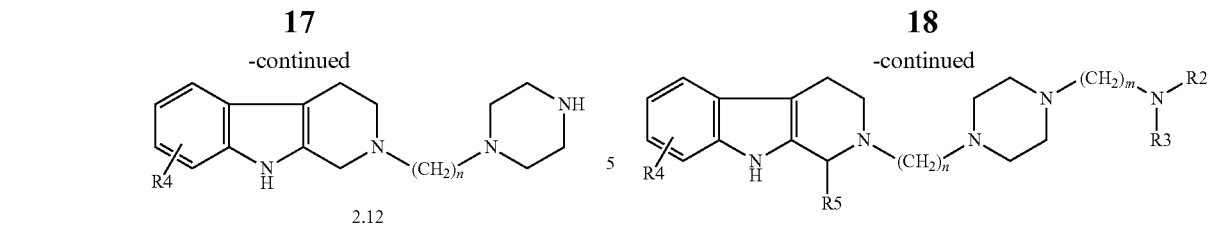

Reagents: (a): K₂CO₃, CH₃CN, reflux; (b): HCl 8%, MeOH.

Scheme 3: Preparation of compounds of the invention
Scheme 3a: Amino side chain on the C-ring of the tricyclic compounds

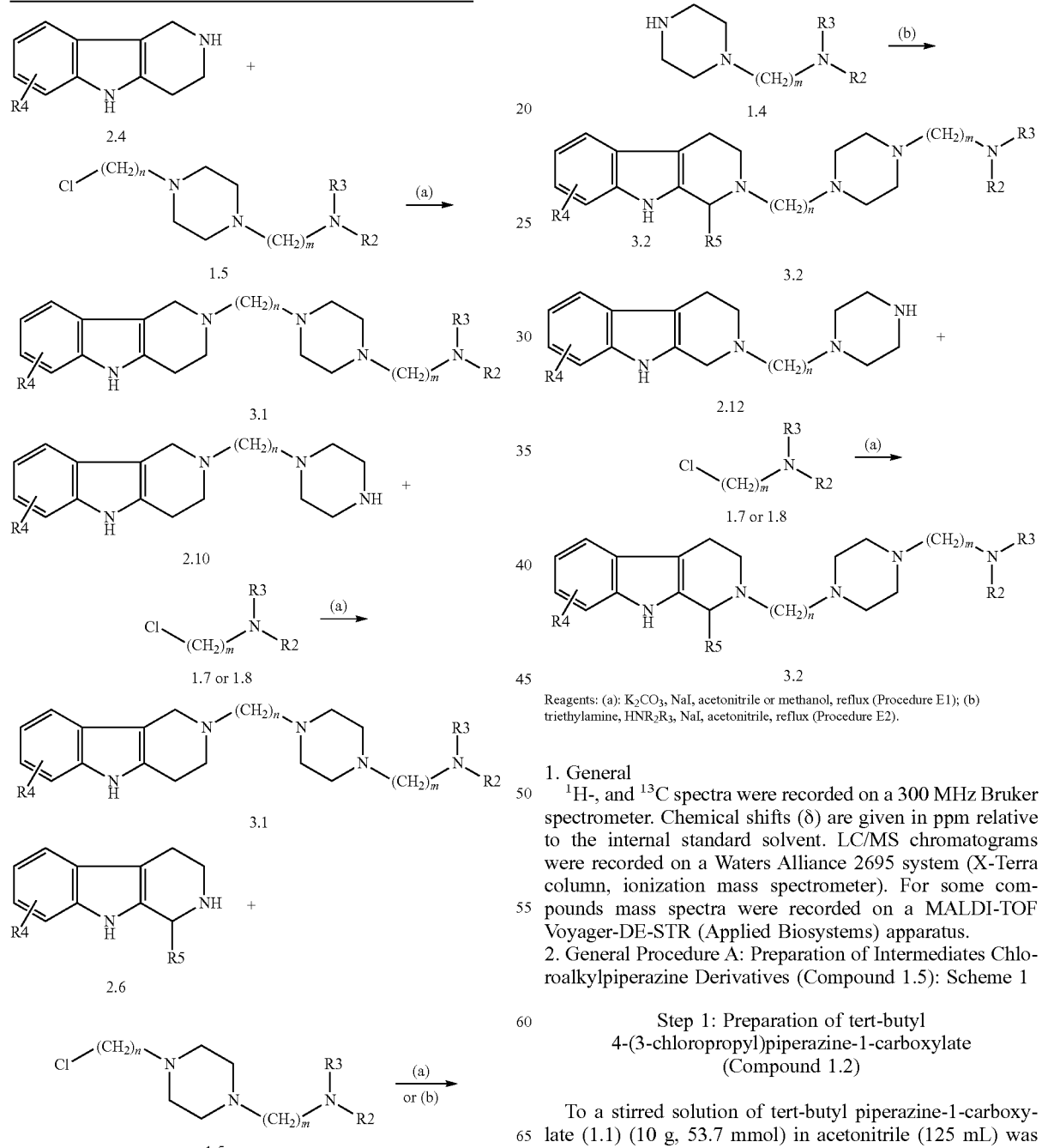

Reagents: (a): K₂CO₃, NaI, acetonitrile or methanol, reflux (Procedure E1); (b) triethylamine, HNR₂R₃, NaI, acetonitrile, reflux (Procedure E2).

1. General $^1$H-, and $^{13}$C spectra were recorded on a 300 MHz Bruker spectrometer. Chemical shifts (δ) are given in ppm relative to the internal standard solvent. LC/MS chromatograms were recorded on a Waters Alliance 2695 system (X-Terra column, ionization mass spectrometer). For some compounds mass spectra were recorded on a MALDI-TOF Voyager-DE-STR (Applied Biosystems) apparatus.

2. General Procedure A: Preparation of Intermediates Chloroalkylpiperazine Derivatives (Compound 1.5): Scheme 1

Step 1: Preparation of tert-butyl 4-(3-chloropropyl)piperazine-1-carboxylate (Compound 1.2)

To a stirred solution of tert-butyl piperazine-1-carboxylate (1.1) (10 g, 53.7 mmol) in acetonitrile (125 mL) was added 1-bromo-3-chloropropane (21.13 g, 134.2 mmol, 2.5 eq), potassium carbonate (7.4 g, 53.7 mmol, 1 eq) and sodium iodide (8.05 g, 53.7 mmol, 1 eq). The mixture was stirred for 24 h at room temperature and the solvent was evaporated. The residue was solubilised again in $CH_2Cl_2$ and basified with 1M NaOH solution. Two layers were separated and the aqueous layer was extracted three times with $CH_2Cl_2$. The combined organic layer was dried with $MgSO_4$ and evaporated under reduced pressure to give the compound 1.2 with a good purity, which was directly used for the next step without purification. MALDI-TOF m/z 263.10-265.14 $[M+H]^+$ Step 2: Preparation of Compounds 1.3

To a stirred solution of tert-butyl 4-(3-chloropropyl)piperazine-1-carboxylate (1.2) (11.35 g, 43.3 mmol, 1 eq) in $CH_2Cl_2$ (400 mL) was added the amine (5 eq), N,N-diisopropylethylamine (5.6 g, 43.3 mmol, 1 eq) and sodium iodide (6.5 g, 43.3 mmol, 1 eq). The mixture was warmed to reflux and stirred for 24 h. The solvent was then evaporated. The residue was solubilised again in $CH_2Cl_2$ and alkalinized with 1M NaOH solution. Two layers were separated and the aqueous layer was extracted three times with $CH_2Cl_2$. The combined organic layer was dried with $MgSO_4$ and evaporated under reduced pressure. The crude was purified by chromatography on silica gel ($CH_2Cl_2$/MeO: 95/5) to give the corresponding compounds 1.3.

Example 1: Preparation of tert-butyl 4-(3-(N,N-diisobutylamino)propyl)piperazine-1-carboxylate (Compound 1.3a)

The compound 1.3a was synthesized according to the procedure described by using N,N-diisobutylamine (27.96 g, 5 eq). Yield: 73%. MALDI-TOF m/z 356.30 $[M+H]^+$ Example 2: Preparation of tert-butyl 4-(3-(N,N-dibenzylamino)propyl)piperazine-1-carboxylate (Compound 1.3b)

The compound 1.3a was synthesized according to the procedure described by using N,N-dibenzylamine (42.7 g, 5 eq). Yield: 49%. LCMS m/z 424.30 $[M+H]^+$ Example 3: Preparation of tert-butyl 4-(3-(pyrrolidin-1-yl)propyl)piperazine-1-carboxylate (Compound 1.3c)

The compound 1.3c was synthesized according to the procedure described by using pyrrolidine (15.4 g, 5 eq). Yield: 80%. LCMS m/z 298.3 $[M+H]^+$ Step 3: Preparation of Compounds 1.4

To a stirred solution of 1.3 (15 mmol) in $CH_2Cl_2$ (80 mL) at room temperature was added trifluoroacetic acid (22.2 mL, 290 mmol, 20 eq). The reaction mixture was stirred overnight and the solvent was removed by evaporation. The residue was basified by using a mixture of saturated $NaHCO_3$ solution and 6M NaOH solution (100/10 v/v), and extracted with $CH_2Cl_2$. The organic layer was dried over $MgSO_4$ and evaporated to give the amine 1.4.

Example 1: Preparation of N,N-diisobutyl-3-(piperazin-1-yl)propylamine (Compound 1.4a)

The compound 1.4a was synthesized from compound 1.3a according to the procedure described. Yield: 96%. MALDI-TOF m/z 256.32 $[M+H]^+$ Example 2: Preparation of N,N-dibenzyl-3-(piperazin-1-yl)propylamine (Compound 1.4b)

The compound 1.4b was synthesized from compound 1.3b according to the procedure described. Yield: 96%. MALDI-TOF m/z 324.08 $[M+H]^+$ Example 3: Preparation of 3-(piperazin-1-yl)propylpyrrolidine (Compound 1.4c)

The compound 1.4c was synthesized from compound 1.3c according to the procedure described. Yield: 90%. LCMS m/z 198.3 $[M+H]^+$ Step 4: Preparation of Chloroalkylpiperazine Derivatives 1.5

To a stirred solution of 1.4 (1 eq) in ethanol at room temperature was added 1-bromoalkyl-1-ol (1.7 eq), potassium carbonate (3 eq) and sodium iodide (1 eq). The reaction mixture was warmed to reflux and stirred for 24 h. Mineral salts were removed by filtration and the filtrate was concentrated under reduced pressure. The crude was solubilised in $CH_2Cl_2$, filtered again to remove residual mineral salts and evaporated. The crude alcohol derivative was solubilised in $CH_2Cl_2$ and cooled to 0° C. Thionylchloride (6 eq) was then added dropwise. After 2 h of stirring at reflux and overnight at room temperature, the solvent was evaporated. The resulting crude was solubilised in a mixture of $CH_2Cl_2$ and water. The aqueous layer was alkalinized and extracted with $CH_2Cl_2$. The organic layer was dried with $MgSO_4$, evaporated and purified by chromatography on silica gel ($CH_2Cl_2$/MeOH: 90/10) to give the chloroalkyl piperazine derivatives 1.5a-d.

Example 1: Preparation of N,N-diisobutyl-3-(4-(3-chloropropyl)piperazin-1-yl)propylamine (Compound 1.5a)

The compound 1.5a was synthesized according to the procedure described by using N,N-diisobutyl-3-(piperazin-1-yl)propylamine (1.4a) and 3-bromopropanol. Yield: 60%. MALDI-TOF m/z 332.3-334.3 $[M+H]^+$ Example 2: Preparation of N,N-dibenzyl-3-(4-(3-chloropropyl)piperazin-1-yl)propylamine (Compound 1.5b)

The compound 1.5b was synthesized according to the procedure described by using N,N-dibenzyl-3-(piperazin-1-yl)propylamine (1.4b) and 3-bromopropanol. Yield: 63%. LCMS m/z 400.24-402.23 $[M+H]^+$ Example 3: Preparation of 3-(4-(3-chloropropyl)piperazin-1-yl)propylpyrrolidine (Compound 1.5c)

The compound 1.5c was synthesized according to the procedure described by using 3-(piperazin-1-yl)propylpyrrolidine (1.4c) and 3-bromopropanol. Yield: 30%. LCMS m/z 274.4-275.2 $[M+H]^+$ Example 4: Preparation of N,N-diisobutyl-3-(4-(2-chloroethyl)piperazin-1-yl)propylamine (Compound 1.5d)

The compound 1.5d was synthesized according to the procedure described by using N,N-diisobutyl-3-(piperazin- 1-yl)propylamine (1.4a) and 2-bromoethanol. Yield: 40%. MALDI-TOF m/z 318.1-320.1 [M+H]$^+$

Preparation of 3-chloro-N,N-diisobutylpropylamine (Compound 1.7)

To a stirred solution of N,N-diisobutylamine (1.6) (3 g, 23.2 mmol) in acetonitrile (150 mL) was added 1-bromo-3-chloropropane (10.90 g, 69.6 mmol, 3 eq), potassium carbonate (6.4 g, 46.4 mmol, 2 eq). The mixture was stirred for 24 h at room temperature. The inorganic was filtered and the solvent was evaporated. The crude product was purified by column chromatography on silica gel or by preparative TLC (CH$_2$Cl$_2$/MeOH: 90/10) gave the compound 1.7. Yield 18%. LCMS m/z 206.1 [M+H]$^+$.

Preparation of 2-chloro-N,N-diisobutylethylamine (Compound 1.8)

To a stirred solution of N,N-diisobutylamine (1.6) (3 g, 23.2 mmol) in acetonitrile (50 mL) at room temperature was added 2-bromoethanol (4.35 g, 34.8 mmol, 1.5 eq), potassium carbonate (6.4 g, 46.4 mmol, 2 eq). The reaction mixture was warmed to reflux and stirred for 24 h. Mineral salts were removed by filtration and the filtrate was concentrated under reduced pressure. The crude was solubilised in CH$_2$Cl$_2$, filtered again to remove residual mineral salts and evaporated.

The crude alcohol derivative was solubilised in CH$_2$Cl$_2$ and cooled to 0° C. Thionylchloride (13.8 g, 116 mmol, 5 eq) was then added dropwise. After stirring overnight at room temperature, the solvent was evaporated. The product purified by chromatography on silica gel (CH$_2$Cl$_2$/MeOH: 90/10) to give compound 1.8. Yield 37%. LCMS m/z 192.6 [M+H]$^+$.

3. General Procedure B: Preparation of Intermediates Tricycle Gamma-Carboline Derivatives (Compounds 2.3 and 2.4): Scheme 2a

Step 1: Preparation of Compounds 2.3

N-carbethoxy-4-piperidone 2.2 (1 eq) and appropriate phenylhydroxylamine or phenylhydrazine 2.1 (1 eq) were dissolved in absolute ethanol at room temperature, and 12N HCl solution can be added. The reaction mixture was stirred at reflux for 2 h or overnight then cooled to room temperature. Treatment of resulting mixture according a suitable procedure gave the corresponding products.

Example 1: Preparation of ethyl 1,3,4,5-tetrahydro-1H-pyrido[4,3-b]indole-2(5H)-carboxylate (Compound 2.3a)

The compound 2.3a was synthesized according to the procedure described by using N-carbethoxy-4-piperidone and phenylhydrazine. The resulting mixture was cooled to room temperature and filtered. Yield 90%. LCMS m/z 245.12 [M+H]$^+$

Example 2: Preparation of ethyl 8-methoxy-1,3,4,5-tetrahydro-1H-pyrido[4,3-b]indole-2(5H)-carboxylate (Compound 2.3b)

The compound 2.3b was synthesized according to the procedure described by using N-carbethoxy-4-piperidone and 4-methoxyphenylhydrazine at reflux for 2 h. After evaporation of solvent, the residue was hydrolysed by water and extracted with ethyl acetate. The organic layer was dried with MgSO$_4$, evaporated and purified by preparative TLC (CH$_2$Cl$_2$/MeOH: 98/2). Yield 93%. LCMS m/z 275.37 [M+H]$^+$

Example 3: Preparation of ethyl 8-methyl-1,3,4,5-tetrahydro-1H-pyrido[4,3-b]indole-2(5H)-carboxylate (Compound 2.3c)

The compound 2.3c was synthesized according to the procedure described by using N-carbethoxy-4-piperidone and 4-methylphenylhydrazine at reflux overnight. The resulting mixture was cooled to room temperature and filtered. Yield 98%. LCMS m/z 259.15 [M+H]$^+$

Example 4: Preparation of ethyl 8-fluoro-1,3,4,5-tetrahydro-1H-pyrido[4,3-b]indole-2(5H)-carboxylate (Compound 2.3d)

The compound 2.3d was synthesized according to the procedure described by using N-carbethoxy-4-piperidone and 4-fluorophenylhydrazine at reflux for 2 h. After evaporation of solvent, the residue was hydrolysed by water and extracted with ethyl acetate. The organic layer was dried with MgSO$_4$ and evaporated and purified by preparative TLC (CH$_2$Cl$_2$/MeOH: 98/2). Yield 75%. LCMS m/z 263.23 [M+H]$^+$

Step 2: Preparation of Compounds 2.4

To solution of 2.3 (13 mmol, in 30 mL ethanol), was added a solution of KOH (15 eq, in 60 mL of ethanol/H$_2$O 6/1 v/v). The reaction mixture was stirred for 15 or 24 hours at reflux then allowed to cool to room temperature. The solvent was removed under reduced pressure. The residue was washed with 1M NaOH solution and extracted with CH$_2$Cl$_2$. The organic layer was dried with MgSO$_4$ and the solvent was evaporated to afford compound 2.4.

Example 1: Preparation of 2,3,4,5-tetrahydro-1H-pyrido[4,3-b]indole (Compound 2.4a)

The compound 2.4a was synthesized according to the procedure described by using ethyl-1,3,4,5-tetrahydro-1H-pyrido[4,3-b]indole-2(5H)-carboxylate (2.3a) at reflux for 15 h. Yield: 35%. LCMS m/z 172.95 [M+H]$^+$

Example 2: Preparation of 8-methoxy-2,3,4,5-tetrahydro-1H-pyrido[4,3-b]indole (Compound 2.4b)

The compound 2.4b was synthesized according to the procedure described by using ethyl-1,3,4,5-tetrahydro-1H-pyrido[4,3-b]indole-2(5H)-carboxylate (2.3b) at reflux for 15 h. Yield: 78%. LCMS m/z 203.21 [M+H]$^+$

Example 3: Preparation of 8-methyl-2,3,4,5-tetrahydro-1H-pyrido[4,3-b]indole (Compound 2.4c)

The compound 2.4c was synthesized according to the procedure described by using ethyl-8-methyl-1,3,4,5-tetrahydro-1H-pyrido[4,3-b]indole-2(5H)-carboxylate (2.3c) at reflux for 15 h. Yield: 75%. LCMS m/z 187.12 [M+H]$^+$

Example 4: Preparation of 8-fluoro-2,3,4,5-tetrahydro-1H-pyrido[4,3-b]indole (Compound 2.4d)

The compound 2.4d was synthesized according to the procedure described by using ethyl-8-fluoro-1,3,4,5-tetrahydro-1H-pyrido[4,3-b]indole-2(5H)-carboxylate (2.3d) at reflux for 15 h. Yield: 46%. LCMS m/z 191.12 [M+H]$^+$ 4. General Procedure C: Preparation of Intermediates Tricycle Beta-Carboline Derivatives (Compounds 2.6 and 2.7): Scheme 2a

Example 1: Preparation of 1-phenyl-2,3,4,9-tetrahydro-1H-beta-carboline (2.6b)

To a stirred solution of tryptamine (5 g, 31.2 mmol) in dichloromethane (70 mL) was added trifluoroacetic acid (3.6 mL, 46.8 mmol, 1.5 eq), and benzaldehyde (4 mL, 46.8 mmol, 1.5 eq). The mixture was stirred for 48 h at room temperature and the solvent was evaporated. The residue was washed with diethyl ether, ethyl acetate and filtered to give the compound 2.6b with a good purity, which was directly used for the next step without purification. Yield: 71%. LCMS m/z 249.13 [M+H]$^+$ General Procedure for the Preparation of Compounds 2.7

To a stirred solution of compounds 2.6 (1 eq) in acetonitrile (50 mL) was added 1-bromo-3-chloropropane (2 eq), potassium carbonate (3 eq). The mixture was stirred for 3 days at room temperature, the mineral was filtered and the solvent was evaporated and purified by chromatography on silica gel (cyclohexane/ethyl acetate: 9.5/0.5).

Example 1: Preparation of 2-(3-chloropropyl)-2,3,4,9-tetrahydro-1H-beta-carboline (Compound 2.7a)

The compound 2.7a was synthesized according to the procedure described by using 2,3,4,9-tetrahydro-1H-beta-carboline (2.6a) (3 g, 17.4 mmol) and 1-bromo-3-chloropropane (3.4 mL, 2 eq). Yield 77%. LCMS m/z 249.4-251.3 [M+H]$^+$

Example 2: Preparation of 2-(3-chloropropyl)-1-phenyl-2,3,4,9-tetrahydro-1H-beta-carboline (Compound 2.7b)

The compound 2.7b was synthesized according to the procedure described above by using 1-phenyl-2,3,4,9-tetrahydro-1H-beta-carboline (2.6b) (3 g, 8.6 mmol) and 1-bromo-3-chloropropane (1.7 mL, 2 eq). Yield 53%. LCMS m/z 325.6-327.2 [M+H]$^+$

Example 3: Preparation of 2-(2-chloroethyl)-1-phenyl-2,3,4,9-tetrahydro-1H-beta-carboline hydrochloride (Compound 2.7c)

Step 1: 2-(1-Phenyl-2,3,4,9-tetrahydro-1H-beta-carbolin-2-yl)ethanol

To a solution of acetonitrile (50 mL), 1-phenyl-2,3,4,9-tetrahydro-1H-beta-carboline (2.6b) (3.0 g, 8.6 mmol), potassium carbonate (3.5 g, 3 eq) and 2-bromoethanol (1.6 mL, 2 eq) was added. The mixture was refluxed for 24 h, filtered and evaporated under reduced pressure. The residue was purified by column chromatography on silica gel (CH$_2$Cl$_2$/methanol: 99.8/0.2). Yield 74%; LCMS m/z 293.2 [M+H]$^+$

Step 2: 2-(2-Chloroethyl)-1-phenyl-2,3,4,9-tetrahydro-1H-beta-carboline hydrochloride To a solution of dichloromethane (150 mL), 2-(1-phenyl-2,3,4,9-tetrahydro-beta-carbolin-2-yl)ethanol was added (3.0 g, 10 mmol). The solution was cooled to 0° C. and thionyl chloride (2.2 mL, 30 mmol) was added dropwise. The mixture was stirred for 4 h at room temperature and evaporated under reduced pressure. The residue was washed with a 5% aqueous solution of potassium carbonate (100 mL) and extracted with dichloromethane. The organic layers were combined, dried over MgSO$_4$, and concentrated under reduced pressure. The residue was purified by column chromatography on silica gel (dichloromethane/methanol 99/1) to afford the corresponding compound 2.7c. The oily product was solubilized in ethyl acetate, then diethyl ether (20 mL) saturated with gaseous hydrochloric acid was added. The precipitate was filtered and washed with ethyl acetate to afford compound 2.7c. Yield 84%; LCMS m/z 311.1-313.2 [M+H]$^+$ 5. General Procedure D: Preparation of Intermediates Tricycle Beta- and Gamma-Carboline Derivatives (Compounds 2.9, 2.10, 2.11, 2.12): Scheme 2b

Preparation of tert-butyl 4-(3-(8-methoxy-1,3,4,5-tetrahydro-1H-pyrido[4,3-b]indol-2-yl)propyl)piperazine-1-carboxylate (Compound 2.9)

To a solution of 8-methoxy-1H,2H,3H,4H,5H-pyrido[4,3-b]indole 2.4 (1.3 g, 6.43 mmol)) in acetonitrile (20 mL) was added the tert-butyl 4-(3-chloropropyl)piperazine-1-carboxylate 1.2 (1.69 g, 6.43 mmol) and K$_2$CO$_3$ (1.33 g, 9.64 mmol). After being stirred for 24 h at reflux, the mineral was filtered and the solvent removed under reduced pressure. The crude product was purified by column chromatography on silica gel or by preparative TLC (CH$_2$Cl$_2$/MeOH: 90/10) gave the compound 2.9. Yield 49%. $^1$H NMR (300 MHz, CDCl$_3$) δ=1.47 (s, 12H), 1.82 (m, 2H), 2.32-2.48 (m, 6H), 2.63 (m, 4H), 2.79 (t, 2H, J=5.4 Hz), 3.42 (m, 4H), 3.67 (s, 2H), 3.82 (s, 3H), 6.70 (dd, 1H, J=2.4 Hz, J=8.8 Hz), 6.83 (d, 1H, J=2.4 Hz), 7.00 (d, 1H, J=8.8 Hz), 8.75 (s, 1H). LCMS m/z 429.1 [M+H]$^+$.

Preparation of 1-(3-(8-methoxy-1,3,4,5-tetrahydro-1H-pyrido[4,3-b]indol-2-yl)propyl)piperazine (Compound 2.10)

To a stirred solution of 2.9 (900 mg, 2.1 mmol) in MeOH (50 mL) at room temperature was added HCl 8% (10 mL). The reaction mixture was stirred overnight and the solvent was removed by evaporation. The crude product was purified by column chromatography on silica gel or by preparative TLC (CH$_2$Cl$_2$/MeOH (saturated with gaseous NH$_3$): 90/10) gave the compound 2.10. Yield 94%. $^1$H NMR (300 MHz, MeOD) δ=2.12 (m, 2H), 2.52 (t, 2H, J=6.4 Hz), 2.78 (m, 4H), 3.18-3.28 (m, 6H), 3.45 (t, 2H, J=8.0 Hz), 3.72 (t, 2H, J=6.0 Hz), 3.83 (s, 3H), 4.53 (s, 2H), 6.77 (dd, 1H, J=2.4 Hz, J=8.8 Hz), 6.98 (d, 1H, J=2.4 Hz), 7.24 (d, 1H, J=8.8 Hz). LCMS m/z 329.1 [M+H]$^+$.

Preparation of tert-butyl 4-(3-{1H,2H,3H,4H,9H-pyrido[3,4-b]indol-2-yl}propyl)piperazine-1-carboxylate (Compound 2.11)

To a solution of 1,2,3,4-tetrahydro-9H-pyrido[3,4-b]indole 2.6 (1.57 g, 9.13 mmol) in acetonitrile (20 mL) was added tert-butyl 4-(3-chloropropyl)piperazine-1-carboxylate 1.2 (2.00 g, 7.61 mmol) and K$_2$CO$_3$ (1.57 g, 11.4 mmol). After being stirred for 24 h at reflux, the mineral was filtered and the solvent removed under reduced pressure. The crude product was purified by column chromatography on silica gel or by preparative TLC (CH$_2$Cl$_2$/MeOH: 90/10) gave the compound 2.11. Yield 82%. $^1$H NMR (300 MHz, CDCl$_3$) δ=1.48 (s, 12H), 1.82 (m, 2H), 2.32-2.49 (m, 6H), 2.62 (t, 2H, J=7.4 Hz), 2.85 (m, 4H), 3.45 (m, 4H), 3.62 (s, 2H), 7.01-7.20 (m, 2H), 7.25 (d, 1H, J=8.3 Hz), 7.48 (d, 1H, J=8.3 Hz), 8.00 (s, 1H). LCMS m/z 400.1 [M+H]$^+$.

Preparation of 1-(3-{1H,2H,3H,4H,9H-pyrido[3,4-b]indol-2-yl}propyl)piperazine trihydrochloride (Compound 2.12)

To a stirred solution of tert-butyl 4-(3-{1H,2H,3H,4H,9H-pyrido[3,4-b]indol-2-yl}propyl)piperazine-1-carboxylate 2.11 (900 mg, 2.1 mmol) in MeOH (50 mL) at room temperature was added HCl 8% (10 mL). The reaction mixture was stirred overnight and the solvent was removed by evaporation. The crude product was purified by column chromatography on silica gel or by preparative TLC (CH$_2$Cl$_2$/MeOH (saturated with gaseous NH$_3$): 90/10) gave the compound 2.12. Yield 98%. $^1$H NMR (300 MHz, MeOD) δ=2.12 (m, 2H), 2.61 (t, 2H, J=6.6 Hz), 2.77 (m, 4H), 3.12 (t, 2H, J=5.9 Hz), 3.23 (m, 4H), 3.40 (m, 2H), 3.63 (t, 2H, J=6.0 Hz), 4.48 (s, 2H), 7.05 (t, 1H, J=7.1 Hz), 7.13 (t, 1H, J=7.0 Hz), 7.36 (d, 1H, J=8.1 Hz), 7.47 (d, 1H, J=7.8 Hz). LCMS m/z 299.0 [M+H]$^+$.

6. General Procedure E: Synthesis of Compounds of the Invention—Scheme 3

General Procedure E1:

To a solution of tricyclic compounds (2.4, 2.6, 2.10 or 2.12) (1 eq) in acetonitrile (20 mL) was added the desired derivative (1.5, 1.7, 1.8) (2 eq), K$_2$CO$_3$ (5 eq) and NaI (1 eq). After being stirred for 24 h at reflux, the solvent was removed under reduced pressure. The residue was solubilised in a mixture of dichloromethane and 1M NaOH solution. The aqueous layer was extracted with dichloromethane. The combined organic layer was dried over MgSO$_4$ and concentrated. The crude was purified by column chromatography on silica gel or by preparative TLC (CH$_2$Cl$_2$/MeOH: 90/10) gave the compounds (3.1, 3.2).

General Procedure E2:

To a solution of tricyclic compound 2.6, 2.7 (1 eq) in acetonitrile (20 mL) was added the desired alkylamine derivative 1.5 (1 eq), triethylamine (5 eq) and NaI (1 eq). After being stirred for at 70° C. or 50° C., the solvent was removed under reduced pressure. The residue was solubilised in a mixture of dichloromethane and 1M NaOH solution. The aqueous layer was extracted with dichloromethane. The combined organic layer was dried over MgSO$_4$ and concentrated. The crude was purified by column chromatography on silica gel or by preparative TLC (CH$_2$Cl$_2$/MeOH: 90/10) gave the compound 3.2.

Example 1: Synthesis of N,N-diisobutyl-3-[4-(3-(1,3,4,5-tetrahydro-1H-pyrido[4,3-b]indol-2-yl)propyl)piperazin-1-yl]propylamine (Compound 3.1a)

Compound 3.1a was synthesized according to the procedure E1 by using 2,3,4,5-tetrahydro-1H-pyrido[4,3-b]indole 2.4a (155 mg, 0.90 mmol, 1 eq) and N,N-diisobutyl-3-(4-(3-chloropropyl)piperazin-1-yl)propylamine 1.5a (300 mg, 0.90 mmol). Yield 76%. $^1$H NMR (300 MHz, MeOD) δ=0.89 (d, 12H, J=6.6 Hz), 1.79-1.52 (m, 4H), 2.00-1.79 (m, 2H), 2.07 (d, 4H, J=7.2 Hz), 2.81-2.19 (m, 16H), 2.93 (t, 4H, J=3.0 Hz), 3.75 (s, 2H), 7.16-6.83 (m, 2H), 7.50-7.16 (m, 2H); MALDI-TOF m/z 468.36 [M+H]$^+$.

Example 2: Synthesis of N,N-diisobutyl-3-(4-(3-(8-methoxy-1,3,4,5-tetrahydro-1H-pyrido[4,3-b]indol-2-yl)propyl)piperazin-1-yl)propylamine (Compound 3.1b)

Compound 3.1b was synthesized according to the procedure E1 by using 8-methoxy-2,3,4,5-tetrahydro-1H-pyrido[4,3-b]indole 2.4b (50 mg, 0.25 mmol) and N,N-diisobutyl-3-(4-(3-chloropropyl)piperazin-1-yl)propylamine 1.5a (82 mg, 0.25 mmol). Yield 52%. $^1$H NMR (300 MHz, MeOD) δ=0.92 (s, 12H), 1.58-1.70 (m, 4H), 1.85 (quint, 2H, J=7 Hz), 2.05 (s, 4H), 2.32-2.52 (m, 16H), 2.88 (s, 3H), 3.66 (s, 2H), 6.76 (td, 1H, J=9 Hz, J=2 Hz), 6.99 (dd, 1H, J=9 Hz, J=2 Hz), 7.19 (dd, 1H, J=9 Hz, J=4 Hz); LCMS m/z 498.54 [M+H]$^+$ Example 3: Synthesis of N,N-diisobutyl-3-[4-(3-(8-methyl-1,3,4,5-tetrahydro-1H-pyrido[4,3-b]indol-2-yl)propyl)piperazin-1-yl]propylamine (Compound 3.1c)

Compound 3.1c was synthesized according to the procedure E1 by using 8-methyl-2,3,4,5-tetrahydro-1H-pyrido[4,3-b]indole 2.4c (56 mg, 0.30 mmol, 1 eq) and N,N-diisobutyl-3-(4-(3-chloropropyl)piperazin-1-yl)propylamine 1.5a (100 mg, 0.30 mmol). Yield 17%. $^1$H NMR (300 MHz, MeOD) δ=0.89 (d, 12H, J=6 Hz), 1.58-1.77 (m, 4H), 1.90 (m, 2H). 2.07 (d, 4H, J=6 Hz), 2.26-2.71 (m, 19H), 2.91 (t, 4H, J=3 Hz), 3.71 (s, 2H), 6.86 (m, 2H), 7.13 (d, 1H, J=8 Hz); MALDI-TOF m/z 482.4 [M+H]$^+$ Example 4: Synthesis of N,N-diisobutyl-3-(4-(3-(8-fluoro-1,3,4,5-tetrahydro-1H-pyrido[4,3-b]indol-2-yl)propyl)piperazin-1-yl)propylamine (Compound 3.1d)

Compound 3.1d was synthesized according to the procedure E1 by using 8-fluoro-2,3,4,5-tetrahydro-1H-pyrido[4,3-b]indole 2.4d (57 mg, 0.30 mmol) and N,N-diisobutyl-3-(4-(3-chloropropyl)piperazin-1-yl)propylamine 1.5a (100 mg, 0.30 mmol). Yield 27%. $^1$H NMR (300 MHz, MeOD) δ=0.88 (s, 12H), 1.58-1.70 (m, 4H), 1.85 (quint, 2H, J=7 Hz), 2.05 (s, 4H), 2.32-2.52 (m, 16H), 2.88 (s, 3H), 3.66 (s, 2H), 6.76 (td, 1H, J=9 Hz, J=2 Hz), 6.99 (dd, 1H, J=9 Hz, J=2 Hz), 7.19 (dd, 1H, J=9 Hz, J=4 Hz); LCMS m/z 486.41 [M+H]$^+$ Example 5: Synthesis of 8-Fluoro-2-{3-[4-(3-(pyrrolidin-1-yl)propyl)piperazin-1-yl]propyl}-2,3,4,5-tetrahydro-1H-pyrido[4,3-b]indole (Compound 3.1f)

Compound 3.1f was synthesized according to procedure E1 by using 8-fluoro-2,3,4,5-tetrahydro-1H-pyrido[4,3-b]indole 2.4d (79.5 mg, 0.418 mmol) and 3-(4-(3-chloropropyl)piperazin-1-yl)propylpyrrolidine (1.5c) (114.5 mg, 0.418 mmol). Yield 85%. $^1$H NMR (300 MHz, MeOD) δ=1.85 (quint, 2H, J=7 Hz), 2.0-2.1 (m, 8H), 2.3-2.4 (m, 2H), 2.4-2.7 (m, 10H), 3.0-3.3 (m, 10H), 4.12 (s, 2H), 6.86

(td, 1H, J=9 Hz, J=2 Hz), 7.11 (dd, 1H, J=9 Hz, J=2 Hz), 7.28 (dd, 1H, J=9 Hz, J=4 Hz); LCMS m/z 428.5 [M+H]$^+$

Example 6: Synthesis of N,N-diisobutyl-2-(4-(3-(8-methoxy-1,3,4,5-tetrahydro-1H-pyrido[4,3-b]indol-2-yl)propyl)piperazin-1-yl)ethylamine (Compound 3.1g)

Compound 3.1g was synthesized according to the procedure E1 by using 1-(3-(8-methoxy-1,3,4,5-tetrahydro-1H-pyrido[4,3-b]indol-2-yl)propyl)piperazine 2.10 (200 mg, 0.609 mmol) and 2-chloroethyl-N,N-diisobutylamine hydrochloride (278 mg, 1.218 mmol). Yield 28%. $^1$H NMR (300 MHz, MeOD) δ=0.94 (d, 12H, J=6.6 Hz), 1.70 (m, 2H), 1.84 (m, 2H), 2.13 (d, 4H, J=7.2 Hz), 2.40-2.61 (m, 14H), 2.70 (t, 4H, J=7.6 Hz), 2.90 (m, 4H), 3.72 (s, 2H), 3.80 (s, 3H), 6.71 (dd, 1H, J=8.7 Hz, J=2.4 Hz), 6.87 (d, 1H, J=2.3 Hz), 7.16 (d, 1H, J=8.7 Hz). $^{13}$C NMR (80 MHz, MeOD) δ=20.3, 23.3, 23.7, 26.9, 49.9, 51.0, 52.4, 52.8, 53.2, 55.3, 56.1, 56.5, 56.6, 64.6, 99.3, 106.2, 110.1, 111.0, 126.1, 131.8, 132.5, 153.7. LCMS m/z 484.2 [M+H]$^+$.

Example 7: Synthesis of N,N-dibenzyl-3-(4-(3-(8-fluoro-1,3,4,5-tetrahydro-1H-pyrido[4,3-b]indol-2-yl)propyl)piperazin-1-yl)propylamine (Compound 3.1h)

Compound 3.1h was synthesized according to the procedure E2 by using 8-fluoro-2,3,4,5-tetrahydro-1H-pyrido[4,3-b]indole 2.4d (80 mg, 0.418 mmol) and N,N-dibenzyl-3-(4-(3-chloropropyl)piperazin-1-yl)propylamine 1.5b (228 mg, 0.418 mmol). Yield 70%. $^1$H NMR (300 MHz, MeOD) δ=1.70 (m, 2H), 1.90 (m, 2H), 2.20-2.60 (m, 22H), 2.80 (s, 4H), 6.80 (m, 1H), 7.04 (m, 1H), 7.20-7.40 (m, 11H). LCMS m/z 554.50 [M+H]$^+$.

Example 8: Synthesis of 3-(4-(3-(8-methoxy-1,3,4,5-tetrahydro-1H-pyrido[4,3-b]indol-2-yl)propyl) piperazin-1-yl)propylpiperidine (Compound 3.1i)

Compound 3.1i was synthesized according to the procedure E1 by using 1-(3-(8-methoxy-1,3,4,5-tetrahydro-1H-pyrido[4,3-b]indol-2-yl)propyl)piperazine 2.10 (200 mg, 0.609 mmol) and commercially 3-chloropropylpiperidine hydrochloride (241 mg, 1.22 mmol). Yield 27%. $^1$H NMR (300 MHz, MeOD) δ=1.70 (m, 2H), 1.90 (m, 4H), 2.10 (m, 2H), 2.25 (m, 2H), 2.82 (m, 2H), 2.91-3.30 (m, 18H), 3.45 (t, 2H, J=7.9 Hz), 3.74 (t, 2H, J=6.0 Hz), 3.83 (s, 3H), 4.55 (s, 2H), 6.79 (dd, 1H, J=8.7 Hz, J=2.5 Hz), 7.01 (d, 1H, J=2.3 Hz), 7.26 (d, 1H, J=8.73 Hz). LCMS m/z 454.1 [M+H]$^+$ Example 9: Synthesis of N,N-diisobutyl-3-{4-[3-(1-phenyl-1,3,4,9-tetrahydro-1H-beta-carbolin-2-yl) propyl]piperazin-1-yl}propylamine (Compound 3.2a)

Compound 3.2a was synthesized according to the procedure E1 by using 1-phenyl-2,3,4,9-tetrahydro-1H-beta-carboline 2.6b (250 mg, 0.77 mmol) and N,N-diisobutyl-3-(4-(3-chloropropyl)piperazin-1-yl)propylamine 1.5a (500 mg, 1.5 mmol). Yield 33%. $^1$H NMR (300 MHz, DMSO-d$_6$), δ=1.00 (t, 12H, CH$_3$, J=6.6 Hz), 2.00 (2, 6H, CH$_2$), 3.30 (m, 24H, CH$_2$), 6.00 (s, 1H, CH), 7.30 (m, 9H, H$_5$, H$_6$, H$_7$, H$_8$, H$_{Ar}$), 9.60 (s, 1H, NH), 10.90 (br s, 2H, NH$^+$). LCMS m/z 544.41 [M+H]$^+$ Example 10: Synthesis of N,N-diisobutyl-3-{4-[3-(6-chloro-1,3,4,9-tetrahydro-1H-beta-carbolin-2-yl) propyl]piperazin-1-yl}propylamine (Compound 3.2b)

Compound 3.2b was synthesized according to the procedure E1 by using 6-chloro-1-phenyl-2,3,4,9-tetrahydro-1H-beta-carboline 2.6c (300 mg, 0.83 mmol) and N,N-diisobutyl-3-(4-(3-chloropropyl)piperazin-1-yl)propylamine 1.5a (530 mg, 1.6 mmol). The compound was salified as a chlorhydrate. Yield 15%. $^1$H NMR (300 MHz, DMSO-d$_6$), δ=1.00 (m, 12H, CH$_3$); 2.20 (M, 6H, CH$_2$, CH); 2.90-3.75 (M, 24H, CH$_2$, NCH$_2$); 4.50 (s, 2H, H$_1$); 6.80 (d, 1H, H$_7$, J=8.1 Hz); 7.00 (d, 1H, H$_8$, J=8.1 Hz); 7.20 (s, 1H, H$_5$); 9.80 (s, 1H, NH); 10.80 (s, 1H, NH$^+$); 11.20 (s, 1H, NH$^+$); 12.20 (s, 1H, NH$^+$). LCMS m/z 502.3-504.4 [M+H]$^+$ Example 11: Synthesis of N,N-dimethyl-3-(4-(3-(1,3,4,9-tetrahydro-1H-beta-carbolin-2-yl)propyl)piperazin-1-yl)propylamine (Compound 3.2d)

Compound 3.2d was synthesized according to the procedure E2 by using 2-(3-chloropropyl)-2,3,4,9-tetrahydro-1H-beta-carboline 2.7a (375 mg, 1.5 mmol) and N,N-dimethyl-3-piperazin-1-ylpropylamine (0.30 mL, 1.5 mmol). Yield 45%. $^1$H NMR (300 MHz, DMSO-d$_6$) δ=2.10 (m, 2H, CH$_2$), 2.30 (m, 2H, CH$_2$), 2.75 (s, 6H, CH$_3$), 3.05 (m, 2H, CH$_2$), 3.15 (m, 8H, CH$_2$), 3.40-3.70 (m, 8H, CH$_2$), 4.50 (m, 2H, CH$_2$), 7.05-7.15 (m, 2H, H$_6$, H$_7$), 7.35 (d, 1H, H$_5$, J=7.2 Hz), 7.50 (d, 1H, H$_8$, J=8.3 Hz), 10.60 (br s, 1H, NH$^+$), 11.20 (br s, 1H, NH). LCMS m/z 384.4 [M+H]$^+$ Example 12: Synthesis of N,N-dimethyl-3-(4-(3-(1-phenyl-1,3,4,9-tetrahydro-1H-beta-carbolin-2-yl) propyl)piperazin-1-yl)propylamine (Compound 3.2e)

Compound 3.2e was synthesized according to the procedure E2 by using 2-(3-chloropropyl)-1-phenyl-2,3,4,9-tetrahydro-1H-beta-carboline 2.7b (500 mg, 1.5 mmol) and N,N-dimethyl-3-piperazin-1-ylpropylamine (0.30 mL, 1.5 mmol). Yield 37%. $^1$H NMR (300 MHz, DMSO-d$_6$) δ=2.10 (m, 2H, CH$_2$), 2.25 (m, 2H, CH$_2$), 2.75 (s, 6H, CH$_3$), 3.10-3.35 (m, 10H, CH$_2$), 3.70 (m, 6H, CH$_2$), 4.00 (m, 4H, CH$_2$), 6.00 (m, 1H, CH), 7.10 (m, 2H, H$_6$, H$_7$), 7.29 (d, 1H, H$_5$, J=7.7 Hz), 7.52 (m, 5H, H$_{Ar}$), 7.57 (d, 1H, H$_8$, J=7.7 Hz), 10.55 (br s, 1H, NH$^+$), 10.90 (br s, 1H, NH). LCMS m/z 460.5 [M+H]$^+$ Example 13: Synthesis of N,N-diisobutyl-2-{4-[3-(1,3,4,9-tetrahydro-1H-beta-carbolin-2-yl)propyl] piperazin-1-yl}ethylamine (Compound 3.2h)

Compound 3.2h was synthesized according to the procedure E1 by using 1-(3-{1H,2H,3H,4H,9H-pyrido[3,4-b]indol-2-yl}propyl)piperazine dihydrochloride 2.12 (200 mg, 0.49 mmol) and 2-chloroethyl-N,N-diisobutylamine hydrochloride 1.8 (224 mg, 0.98 mmol). Yield 15%. $^1$H NMR (300 MHz, MeOD) δ=0.88 (d, 12H, CH$_3$, J=6.6 Hz), 1.71 (m, 2H, CH), 1.85 (m, 2H, CH$_2$), 2.15 (d, 4H, CH$_2$, J=7.2 Hz), 2.40-2.65 (m, 14H, CH$_2$), 2.72 (t, 2H, CH$_2$, J=7.5 Hz), 2.85 (t, 2H, CH$_2$, J=5.3 Hz), 2.94 (t, 2H, CH$_2$, J=6.1 Hz), 3.75 (s, 2H, CH$_2$), 6.97 (td, 1H, H$_{Ar}$, J=7.8 Hz, J=1.2 Hz), 7.28 (td, 1H, H$_{Ar}$, J=7.0 Hz, J=1.2 Hz), 7.28 (d, 1H, H$_8$, J=7.8 Hz), 7.39 (d, 1H, H$_5$, J=7.5 Hz). LCMS m/z 454.1 [M+H]$^+$.

Example 14: Synthesis of 1-[3-(piperidin-1-yl)propyl]-4-(3-{1H,2H,3H,4H,9H-pyrido[3,4-b]indol-2-yl}propyl)piperazine (Compound 3.2i)

Compound 3.21 was synthesized according to the procedure E1 by using 1-(3-{1H,2H,3H,4H,9H-pyrido[3,4-b]indol-2-yl}propyl)piperazine dihydrochloride 2.12 (200 mg, 0.49 mmol) and commercially 3-chloropropylpiperidine (159 mg, 0.98 mmol). Yield 47%. $^1$H NMR (300 MHz, MeOD) δ=1.50 (m, 2H, $CH_2$), 1.64 (m, 4H, $CH_2$), 1.73 (m, 2H, $CH_2$), 1.83 (m, 2H, $CH_2$), 2.33-2.67 (m, 20H, $CH_2$), 2.85 (m, 4H, $CH_2$), 3.69 (s, 2H, $CH_2$), 6.98 (td, 1H, $H_{Ar}$, J=7.8 Hz, J=1.0 Hz), 7.05 (td, 1H, $H_{Ar}$, J=7.9 Hz, J=1.2 Hz), 7.28 (d, 1H, $H_8$, J=7.8 Hz), 7.39 (d, 1H, $H_5$, J=7.5 Hz). LCMS m/z 424.1 $[M+H]^+$.

Example 15: Synthesis of 1-[2-(piperidin-1-yl)ethyl]-4-(3-{1H,2H,3H,4H,9H-pyrido[3,4-b]indol-2-yl}propyl)piperazine (Compound 3.2j)

Compound 3.2j was synthesized according to the procedure E1 by using 1-(3-{1H,2H,3H,4H,9H-pyrido[3,4-b]indol-2-yl}propyl)piperazine dihydrochloride 2.12 (200 mg, 0.49 mmol) and commercial 2-chloroethylpiperidine (145 mg, 0.98 mmol). Yield 26%. $^1$H NMR (300 MHz, MeOD) δ=1.53 (m, 2H), 1.70 (m, 4H), 1.85 (m, 2H), 2.45-2.67 (m, 12H), 2.69-2.81 (m, 8H), 2.85 (t, 2H, J=5.5 Hz), 2.97 (t, 2H, J=5.2 Hz), 3.78 (s, 2H), 6.98 (td, 1H, $H_{Ar}$, J=7.1 Hz, J=1.1 Hz), 7.06 (td, 1H, $H_{Ar}$, J=7.1 Hz, J=1.2 Hz), 7.29 (d, 1H, $H_8$, J=7.8 Hz), 7.40 (d, 1H, $H_5$, J=7.65 Hz). LCMS m/z 410.1 $[M+H]^+$.

Example 16: Synthesis of N,N-dimethyl-3-(4-(2-(1-phenyl-1,3,4,9-tetrahydro-1H-beta-carbolin-2-yl)ethyl)piperazin-1-yl)propylamine (Compound 3.2k)

Compound 3.2k was synthesized according to the procedure E2 by using 2-(2-chloroethyl)-1-phenyl-2,3,4,9-tetrahydro-1H-beta-carboline 2.7c (500 mg, 1.60 mmol) and commercially N,N-dimethyl-3-piperazin-1-ylpropylamine (0.30 mL, 1.60 mmol). Yield 32%. $^1$H NMR (300 MHz, DMSO-$d_6$) δ=2.20 (m, 2H, $CH_2$), 2.75 (s, 6H, $CH_3$), 3.00-3.50 (m, 18H, $CH_2$), 4.10 (m, 1H, $CH_2$), 4.50 (m, 1H, $CH_2$), 6.10 (s, 1H, CH), 7.10 (m, 2H, $H_6$, $H_7$), 7.30 (d, 1H, $H_8$, J=8.2 Hz), 7.50 (m, 6H, $H_5$, $H_{Ar}$), 10.80 (br s, 1H, NH), 11.00 (br s, 1H, $NH^+$), 11.50 (br s, 1H, $NH^+$), 11.70 (br s, 1H, $NH^+$), 12.20 (br s, 1H, $NH^+$). LCMS m/z 406.7 $[M+H]^+$.

Biological Results

Cell Cultures and Transfections to Test Activity on Aβ1-40 and Aβ1-42 Secretion

Human neuroblastoma cell line SKNSH-SYSY (ATCC® Catalog No. CRL-2266™), HEK (ATCC® CRL-1573™) and COS-1 (ATCC® CRL-1650™) cells were maintained in Dulbecco's modified Eagle medium (DMEM, GIBCO BRL) supplemented with 10% fetal calf serum, 2 mM L-glutamine, 1 mM non-essential amino acids, 50 units/ml penicillin/streptomycin (Invitrogen, France) in a 5% $CO_2$ humidified incubator at 37° C. APP695 cDNA was subcloned into eukaryotic expression vector pcDNA3 (Invitrogen), allowing for a G418 (Invitrogen) selection of clones. This APP cDNA coding for the 695 amino acid long isoform was transfected into SKNSH-SYSY cells using the ethyleneimine polymer ExGen 500 (Euromedex) according to the manufacturer's instructions. The cells expressing APP (SKNSH-SYSY $APP^{WT}$) were selected by the addition of 200 μg/ml G418 in the cell medium. To quantify AR which released in the cell culture medium, the collected medium was spun at 200×g to eliminate the cell debris. The concentrations of secreted $Aâ_{1-40}$ and $Aβ_{1-42}$ were determined using the Human Aβ (1-40) Assay Kit (IBL) or the INNOTEST™ beta-Amyloid (1-42) ELISA Kit (Innogenetics), according to manufacturer's instructions. The results were expressed as $IC_{50}$, i.e. the concentration able to decrease to 50% the basal amount of secreted Aβ peptide 1-40 and 1-42.

Quantifications of APP-CTFs and AICD

After treatment, SY5Y-$APP^{WT}$ cells were scrapped and lysed in 1× Lysis Buffer (250 mM NaCl, 50 mM Tris, pH 8.8, 5 mM EDTA, 2.5% Triton X-100, 1% Deoxycholate, 0.1% SDS). For the Western blotting, an equal amount of total proteins (20 μg/lane) was loaded on a 16.5% Tris-Tricine or 8-16% Tris-Glycine polyacrylamide gel.

SDS-polyacrylamide gel electrophoresis (PAGE) was performed using the Criterion™ Tris-Tricine-precast or Bis-Tris-precast criterion gels (Bio-Rad Bioresearch division). Proteins were transferred to a 0.2 cm$^2$ nitrocellulose membrane (Hybond, Amersham Biosciences) at 2.5 mA/cm2 per gel using the Criterion™ Blotter system (Amersham Biosciences), according to the manufacturer's instructions. Proteins were reversibly stained with Ponceau Red in order to check the quality of the transfer of protein. The membranes were blocked in 25 mM Tris-HCl pH 8.0, 150 mM NaCl, 0.1% Tween-20 (v/v) and 5% (w/v) of skimmed milk for 30 min. Membranes were incubated overnight at 4° C. with appropriate dilution of the primary antibodies, and were incubated for 1 h at room temperature with secondary antibody. The immunoreactive complexes were revealed using the ECL™ Western Blotting kit and LAS-3000 Chemiluminescence Camera acquisition system (FujiFilm). Quantifications were calculated with Image J software (NIH) and the data were collected using Excel Software (Microsoft). The loading variations between Western blot lanes were normalized according to the tubulin signal. Quantification of CTFα and AICD were compared to control conditions (considered as 100 in arbitrary units) and are presented for two concentrations of the drug: 1 and 10 μM.

Cytotoxicity Evaluation

Human neuroblastoma cell line SY5Y-$APP^{WT}$ was used to assess the cytotoxic effects of each compound. SY5Y-$APP^{WT}$ cells were seeded at 20000 cells/well onto 96-well plates and were cultured in Dulbecco's modified Eagle medium (DMEM, Invitrogen) supplemented with 10% fetal calf serum (PAA), 2 mM L-glutamine (Invitrogen), 1 mM non-essential amino acids (Invitrogen), 50 units/ml penicillin/streptomycin (Invitrogen), and 200 μg G418=geneticin (Invitrogen) (selection for cells expressing APP) in a 5% $CO_2$ humidified incubator at 37° C. After 24 h, the cells were washed and incubated with the compound at 0.1; 0.3; 1; 3; 10; 30 and 100 μM or with DMSO as control diluted in the same culture medium at 37° C. in 5% $CO_2$. After 24 h of treatment, cytotoxicity was determined by using colorimetric MTS assay (CellTiter 96® Aqueous One Solution Cell Proliferation Assay-MTS Promega) according to the protocol of the manufacturer. Absorbance was read at 490 nm and results were expressed as % from control condition considered as 100%. $IC_{50}$ is the concentration at which 50% of cells did not survive after a 24 h treatment.

Soluble APPα Quantification

Human neuroblastoma cell line SKNSH-SYSY APP' was cultured in Dulbecco's modified Eagle medium (Invitrogen) supplemented with 10% fetal calf serum (PAA), 2 mM L-glutamine (Invitrogen), 1 mM non-essential amino acids (Invitrogen), 50 units/ml penicillin/streptomycin (Invitrogen), and 200 μg G418=geneticin (Invitrogen) (selection for cell expressing APP) in a 5% $CO_2$ humidified incubator at 37° C. Cells were counted and seed at 400000 cells/well into a 12-wells plate for 24 h. The day after, cells were treated with 700 μL/well of drug at 0.3; 1; 3 and 10 μM and incubated for 24 h in a 5% $CO_2$ incubator at 37° C. After treatment, culture medium samples were collected and stored at −80° C. until analysis. Samples corresponding to the 1 and 10 μM treatment were centrifuged 1500 rpm for 5 min at 4° C. sAPPα quantification by ELISA was done with Human sAPPα Assay Kit-IBL (Cat#27734) in accordance with manufacturer's protocol. Samples were diluted at 1:150 in the diluent buffer provided in the kit. Each sample was loaded in duplicate onto the 96 well-plate. Results are expressed in ng/ml and then compared to control conditions (considered as 100 in arbitrary units) and are presented for two concentrations of the drug: 1 and 10 μM.

In Vivo Acute Treatment

Female C57Bl6 mice of 4 month-old were treated p.o. (gavage) with either vehicle (control) or drug at 3; 6; 12.5 and 25 mg/kg (n=6 per group) for 24 h. The product was administered with a disposable Rodent Feeding Tube ECI-MED Ref#V0104030 (4 mm×30 mm). After 24 h, mice were sacrificed and their troncal blood was collected and stored at 4° C. Brains were immediately removed to dissect the Frontal Cortex, the Cortex around the Hippocampus and the Hippocampus. These areas were stored at −80° C. until use. Blood was then centrifuged at 2100×g for 5 min. Resulting plasma was used to quantify the circulating drug and brain tissues were used for biochemical determinations (PFC: prefrontal cortex and HIP: hippocampus).

In Vivo Chronic Treatment

Female C57Bl6 mice of 4 month-old were treated with either vehicle (control) or drug at 1 and 3 mg/kg (n=10 per group) for 12 weeks in drinking water. First of all, all mice were weighted and distributed in each cage in order to have approximately the same average of weight±SD per cage. Each concentration of product as well as vehicule was prepared in sterile bottles and the bottles were kept at room temperature protected from light. The drinking bottles were filled weekly and weighted. Volume consumed was calculated by weighting each bottle after each week and the remaining volume was discarded. After 12 weeks, mice were sacrificed and their troncal blood was collected and stored at 4° C. Brains were immediately removed to dissect the Frontal Cortex, the Cortex around the Hippocampus and the Hippocampus. These areas were stored at −80° C. until use. Blood was then centrifuged at 2100×g for 5 min. Resulting plasma was used to quantify the circulating drug and brain tissues were used for biochemical determinations (PFC: prefrontal cortex and HIP: hippocampus).

VCP Affinity Evaluation

Biotinylated-Probe Synthesis 4.7

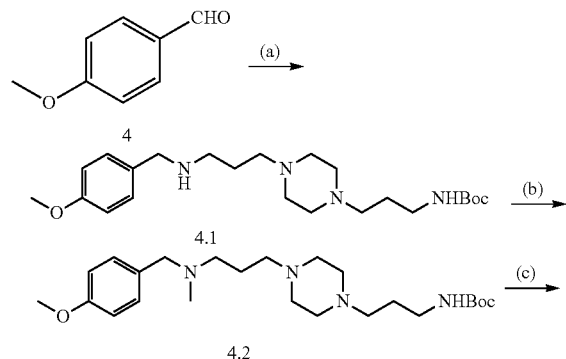

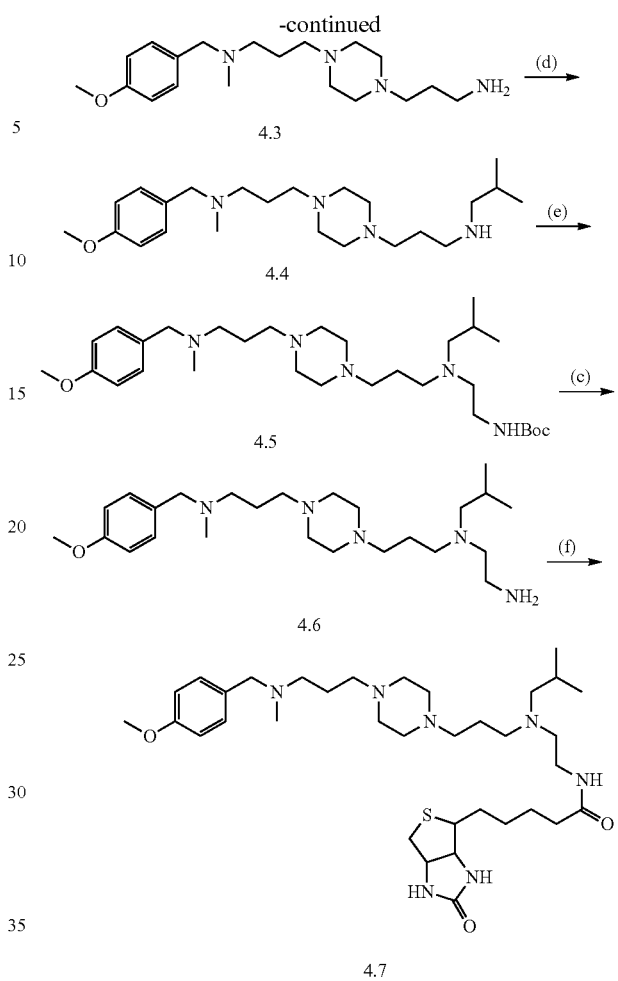

Reagents: (a): tert-butyl 3-(4-(3-aminopropyl)piperazin-1-yl)propylcarbamate, $NaBH_4$, MeOH (b): $HCO_2H$, HCHO, EtOH, reflux; (c): TFA, $CH_2Cl_2$, rt; (d): isobutyraldehyde, $NaBH_4$, MeOH, rt; (e): $OHCCH_2NHBoc$, $NaBH(OAc)_3$, $CH_2Cl_2$, rt; (f): triethylamine, Biotine-OSu, DMF, rt.

Preparation of tert-butyl 3-(4-(3-(4-methoxybenzylamino)propyl)piperazin-1-yl)propyl carbamate (Compound 4.1)

To a stirred solution of tert-butyl 3-(4-(3-aminopropyl) piperazin-1-yl)propylcarbamate (2.7 g, 10 mmol) in methanol (10 mL) at room temperature, in presence of 3 A molecular sieves and under inert atmosphere, was added 4-methoxybenzaldehyde 4 (3.0 g, 11 mmol). The mixture was stirred for 16 h and cooled to 0° C. by using an ice-bath and then $NaBH_4$ (0.95 g, 25 mmol) was added in small portions. After additional 30 minutes of stirring, the mixture was filtered over celite. The filtrate was evaporated; the concentrate was dissolved in $CH_2Cl_2$ and alkalinized with 1M NaOH solution. Two layers were separated and the aqueous layer was extracted with $CH_2Cl_2$. The combined organic layers were dried over $MgSO_4$ and evaporated. Crude compound 4.1 was used for the next step without purification. $^1$H NMR (MeOD, 300 MHz) δ: 1.45 (s, 9H), 1.82-1.61 (m, 4H), 2.65-2.30 (m, 12H), 2.70 (t, 2H, J=6.1 Hz), 3.10 (t, 2H, J=5.9 Hz), 3.49 (s, 2H), 3.80 (s, 3H), 6.91 (m, 2H), 7.28 (m, 2H)). LCMS m/z 421.45 [M+H]$^+$.

Preparation of tert-butyl 3-(4-(3-(N-(4-methoxybenzyl)-N-methylamino)propyl)piperazin-1-yl)propylcarbamate (Compound 4.2)

To a stirred solution of tert-butyl 3-(4-(3-(4-methoxybenzylamino)propyl)piperazin-1-yl)propyl carbamate 4.1 (3.9 g, 10 mmol) in ethanol (50 mL) at room temperature, was added formic acid (0.65 mL, 17 mmol) and formaldehyde 37% (0.35 mL, 5 mmol). The solution was refluxed for 4 h and hydrolyzed with 1M NaOH solution (10 mL). The mixture was extracted with $CH_2Cl_2$. The organic layer was dried over $MgSO_4$ and evaporated. Purification by chromatography on silica gel (eluent: $CH_2Cl_2$/MeOH/$NH_3$ 95/5 v/v) yielded compound 4.2. Yield 49%. $^1$H NMR (MeOD, 300 MHz) δ: 1.47 (s, 9H), 1.83-1.61 (m, 4H), 2.23 (s, 3H), 2.65-2.37 (m, 14H), 3.10 (t, 2H, J=6.6 Hz), 3.49 (s, 2H), 3.80 (s, 3H), 6.90 (d, 2H, J=8.7 Hz), 7.24 (d, 2H, J=8.7 Hz).

Preparation of 3-(4-(3-(N-(4-methoxybenzyl)-N-methylamino)propyl)piperazin-1-yl)propylamine (Compound 4.3)

To a stirred solution of tert-butyl 3-(4-(3-(N-(4-methoxybenzyl)-N-methylamino)propyl)piperazin-1-yl)propylcarbamate 4.2 (3.9 g, 10 mmol) in $CH_2Cl_2$ (50 mL) at room temperature was added TFA (7.7 mL, 100 mmol). The reaction mixture was stirred overnight and the solvent was removed by evaporation. The residue was alkalinized with a mixture of saturated $NaHCO_3$ solution and 6M NaOH solution (80/20 v/v, 50 mL), and extracted with $CH_2Cl_2$. The organic layer was dried over $MgSO_4$ and evaporated to give the corresponding unprotected product 4.3, which was directly used for next step without purification. Yield 98%. $^1$H NMR (MeOD, 300 MHz) δ: 1.82-1.61 (m, 4H), 2.22 (s, 3H), 2.80-2.33 (m, 16H), 3.48 (s, 2H), 3.80 (s, 3H), 6.90 (d, 2H, J=8.7 Hz), 7.24 (d, 2H, J=8.7 Hz).

Preparation of 3-(4-(3-Isobutylaminopropyl)piperazin-1-yl)-N-(4-methoxybenzyl)-N-methylpropan-1-amine (Compound 4.4)

To a stirred solution of 3-(4-(3-(N-(4-methoxybenzyl)-N-methylamino)propyl)piperazin-1-yl)propylamine 4.3 (3.3 g, 10 mmol) in methanol (100 mL) at room temperature, in presence of 3 A molecular sieves and under inert atmosphere, was added isobutyraldehyde (1.0 mL, 11 mmol). The mixture was stirred for 16 h and cooled to 0° C. and then $NaBH_4$ (1.0 g, 25 mmol) was added in small portions. After additional 30 minutes of stirring, the mixture was filtered over celite. The filtrate was evaporated; the concentrate was dissolved in $CH_2Cl_2$ and alkalinized with 1M NaOH solution. Two layers were separated and the aqueous layer was extracted with $CH_2Cl_2$. The combined organic layers were dried over $MgSO_4$ and evaporated. Purification by column chromatography on silica gel ($CH_2Cl_2$/MeOH/$NH_3$ 90/10 v/v) gave the corresponding product 4.4. Yield 58%. $^1$H NMR (MeOD, 300 MHz) δ: 0.92 (d, 6H, J=6.6 Hz), 1.87-1.63 (m, 4H), 2.18 (s, 3H), 2.68-2.23 (m, 16H), 3.44 (s, 2H), 3.76 (s, 3H), 6.87 (d, 2H, J=8.7 Hz), 7.22 (d, 2H, J=8.7 Hz). LCMS m/z 391.41 [M+H]$^+$.

Preparation of tert-butyl 2-(isobutyl(3-(4-(3-(N-(4-methoxybenzyl)-N-methylamino)propyl)piperazin-1-yl)propyl)amino)ethylcarbamate (Compound 4.5)

To a stirred solution of 3-(4-(3-isobutylaminopropyl)piperazin-1-yl)-N-(4-methoxybenzyl)-N-methylpropan-1-amine 4.4 (360 mg, 0.92 mmol) in $CH_2Cl_2$ (20 mL), at room temperature and under inert atmosphere were added CHO—$CH_2$—NHBoc (220 mg, 1.38 mmol) and NaBH(OAc)$_3$ (293 mg, 1.38 mmol). The mixture was stirred for 24 h and 1N NaOH solution (15 mL) was added. After additional 15 minutes of stirring, the resulting mixture was extracted with $CH_2Cl_2$. The organic layer was dried with $MgSO_4$, evaporated and purified by chromatography on silica gel ($CH_2Cl_2$/MeOH/$NH_3$ 95/5 v/v) to give corresponding substituted product 4.5. Yield 71%. $^1$H NMR (MeOD, 300 MHz) δ: 0.92 (d, 6H, J=6.6 Hz), 1.46 (s, 9H), 1.92-1.72 (m, 4H), 2.18 (d, 2H, J=6.9 Hz), 2.23 (s, 3H), 2.81-2.50 (m, 14H), 3.13 (m, 2H), 3.50 (s, 2H), 3.81 (s, 3H), 6.90 (d, 2H, J=7.8 Hz), 7.25 (2H, J=7.8 Hz). LCMS m/z 534.58 [M+H]$^+$.

Preparation of N'-isobutyl-N'-(3-(4-(3-(N-(4-methoxybenzyl)-N-methylamino)propyl)piperazin-1-yl)propyl)ethane-1,2-diamine (Compound 4.6)

To a stirred solution of tert-butyl 2-(isobutyl(3-(4-(3-(N-(4-methoxybenzyl)-N-methylamino)propyl)piperazin-1-yl)propyl)amino)ethylcarbamate 4.5 (0.5 g, 1 mmol) in $CH_2Cl_2$ (30 mL) at room temperature was added TFA (0.8 mL, 10 mmol). The reaction mixture was stirred overnight and the solvent was removed by evaporation. The residue was alkalinized with a mixture of saturated $NaHCO_3$ solution and 6M NaOH solution (80/20 v/v, 10 mL), and extracted with $CH_2Cl_2$. The organic layer was dried over $MgSO_4$ and evaporated to give the corresponding unprotected product 4.6, which was directly used for next step without purification. Yield 98%. $^1$H NMR (MeOD, 300 MHz) δ: 0.92 (d, J=6.9 Hz), 2.19-2.00 (m, 3H), 2.72 (s, 3H), 3.55-3.07 (m, 12H), 3.76 (s, 3H), 4.32-4.14 (m, 2H), 7.32 (d, J=9 Hz, 2H). LCMS m/z 434.50 [M+H]$^+$.

Preparation of N-(2-(isobutyl(3-(4-(3-(N-(4-methoxybenzyl)-N-methylamino)propyl)piperazin-1-yl)propyl)amino)ethyl)-5-(2-oxohexahydro-1H-thieno[3,4-d]imidazol-4-yl)pentanamide (Compound 4.7)

To a solution of N'-isobutyl-N'-(3-(4-(3-(N-(4-methoxybenzyl)-N-methylamino)propyl)piperazin-1-yl)propyl)ethane-1,2-diamine 4.6 (0.3 g, 0.64 mmol) in DMF (10 mL) at room temperature was added triethylamine (1.4 mL, 9.6 mmol) and then Biotine-OSu (219 mg, 0.64 mmol). After being stirred for 24 h at room temperature, the solvent was removed under reduced pressure. Purification of the crude by preparative TLC (eluent: $CH_2Cl_2$/MeOH/$NH_3$ 90/10/2 v/v) gave compound 4.7. Yield 63%. $^1$H NMR (MeOD, 300 MHz) δ: 0.88 (d, J=6.6 Hz, 6H), 1.81-1.10 (m, 12 Hz), 2.19-2.15 (dd, J=7.4 Hz, J=2.1 Hz, 4H), 2.22 (s, 3H), 2.93-2.30 (m, 20H), 3.28-3.12 (m, 2H), 3.49 (s, 2H), 3.79 (s, 3H), 4.30-4.36 (m, 1H), 4.51-4.45 (m, 1H), 6.87 (d, J=6.6 Hz, 2H), 7.22 (d, J=6.6 Hz, 2H). LCMS m/z 660.85 [M+H]$^+$.

VCP Interaction Assay

Physical interaction between HIS-tagged valosin-containing protein/p97 (VCP/p97) (TebuBio) and biotinylated probe 4.7 was investigated by Enzyme-Linked Assay (ELA) based on HIS-Select® High Sensitivity Nickel coated plates, used following manufacturer's recommendations (Sigma Aldrich). Other chemical compounds were tested in competition with the biotinylated probe 4.7 in this system. Briefly, nickel beads were incubated overnight at 4° C. with 2% casein blocking solution. After a three-time rinse with wash buffer (0.05% Tween20 in phosphate buffer saline), HIS-tagged VCP/p97 protein (5 μg/ml in PBS) was incubated with nickel beads for 90 min at 25° C. Then, the plate was washed three times. Chemical compounds (60 μM) were incubated 10 min at 25° C. before addition of biotinylated probe 4.7 (20 μM) 30 min at 25° C. After five washes, streptavidin-peroxidase (2 μg/ml) was added during 1 h at 25° C., followed by the peroxidase substrate addition 30 min at RT. Reaction was stopped with 0.5M $H_2SO_4$ solution and the optical density was read at 450 nm using a microplate reader (VICTOR X4 Wallac, 2030-0040, PerkinElmer). Competition efficiency was quantified by the loss of signal compared to the control condition.

The experimental results of representative compounds are given in the following Table I.

TABLE I

|  | In vitro experiment | | | | | | | Acute In vivo experiment | |
| --- | --- | --- | --- | --- | --- | --- | --- | --- | --- |
|  |  |  |  |  |  |  |  | HIP CTFα | PFC CTFα |
| Ref | $A\beta_{1-40}$ ($IC_{50}$, μM) | $A\beta_{1-42}$ ($IC_{50}$, μM) | $CC_{50}$ (μM) | AICD[a] (10 μM) | CTFα[a] (10 μM) | sAPPα (10 μM) | VCP | (6-12.5 mg/kg) | (6-12.5 mg/kg) |
| 3.1a | 1.2 | 2.1 |  | 1081 | 2875 |  |  |  |  |
| 3.1b |  |  | >10 | 16400 | 100234 |  |  |  |  |
| 3.1c | 1 | 10 | 10 |  | 355 |  |  |  |  |
| 3.1d | 1.2 | 2.1 | 15 | 84225 | 1011 | 166 | 96% | 110 | 90 |
|  |  |  |  |  |  |  |  | 115 | 90 |
| 3.1f | 3 | 1 | >100 | 1011 |  | 100 |  |  |  |
| 3.1g | 2.5 | 3.5 |  |  |  |  |  |  |  |
| 3.1h | 2.5 | 2.5 | 4.8 |  |  |  |  |  |  |
| 3.1i | 10 | >10 | >100 |  |  |  |  |  |  |
| 3.2a | 2 | 5 |  |  |  |  |  |  |  |
| 3.2b |  | >10 | >100 | 7417 | 716 |  |  |  |  |
| 3.2d | >10 | >10 | >100 | 41661 | 1042 |  | 70% |  |  |
| 3.2e | 2.5 | 2 | 12 | 4765 | 234 |  |  |  |  |
| 3.2h | 3 | 3 |  |  |  |  |  |  |  |
| 3.2i | 5 | 5 | >100 |  |  |  |  |  |  |
| 3.2j | 5 | 3 | >100 |  |  |  |  |  |  |

[a]Results in arbitrary units compared to a control (no active ingredient added) with a value of 100.
HIP: hippocampus
PFC: prefrontal cortex In the chronic treatment, the less toxic and metabolically more stable compound 3.1f provided an increase of CTFα of 20% in prefrontal cortex (PFC) and 25% in hippocampus (HIP) at the 3 mg/kg dose.

The invention claimed is:

1. A compound according to Formula (A)

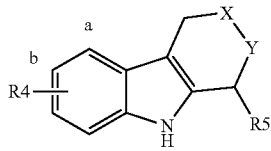

(A)

or a pharmaceutically acceptable salt, solvate, hydrate or polymorph thereof, wherein X and Y are different from one another and are selected from:

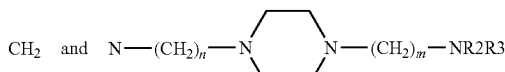

wherein n and m are independently selected from 2 and 3;

R2 and R3 are selected independently from one another from the groups consisting of:

linear or branched ($C_1$-$C_{12}$) alkyl;

benzyl optionally substituted with an alkyl group, halogen, an ether group and/or a $NH_2$ group; or R2 and R3 form together with the nitrogen atom carrying them one of the following heterocyclic groups:

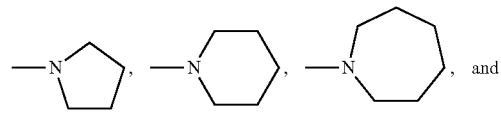, and

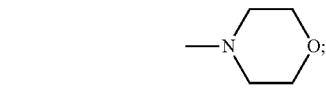;

R4 is selected from F, Cl, H, O—$CH_3$, and —$CH_3$;

R5 is selected from H, $CH_3$ and a phenyl group;

with the proviso that R5 is H if X is not $CH_2$.

2. A compound according to claim 1, wherein R2 and R3 are identical and are selected from ($C_1$-$C_{12}$) alkyls.

3. A compound according to claim 1, wherein R2 and R3 are identical and either isobutyl or methyl groups.

4. A compound according to claim 1, wherein R4 is attached to the carbon atom in position b and is selected from F, Cl, H and O—$CH_3$.

5. A compound according to claim 1, wherein R2, R3 and the nitrogen atom carrying them form one of the following heterocyclic groups:

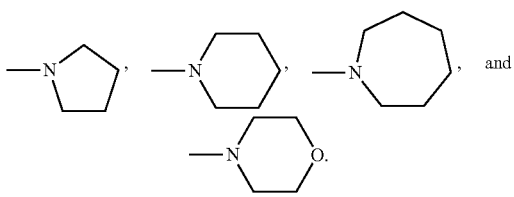

6. A compound according to claim 1, wherein R2 and R3 and the nitrogen atom carrying them form a pyrrolidinyl group.

7. A compound or a pharmaceutically acceptable salt, solvate, hydrate or polymorph thereof according to claim 1, wherein the compound has Formula (I):

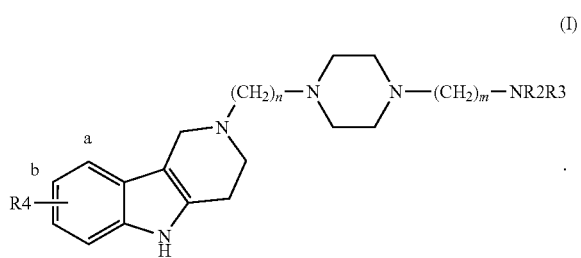

8. A compound or a pharmaceutically acceptable salt, solvate, hydrate or polymorph thereof according to claim 1, wherein the compound has Formula (II):

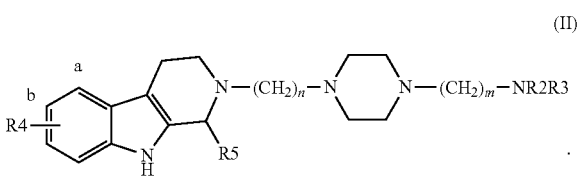

9. A compound according to claim 1 selected from the group consisting of:
N,N-diisobutyl-3-[4-(3-(1,3,4,5-tetrahydro-1H-pyrido[4,3-b]indol-2-yl)propyl)piperazin-1-yl]propylamine,
N,N-diisobutyl-3-(4-(3-(8-m ethoxy-1,3,4,5-tetrahydro-1H-pyrido[4, 3-b]indol-2-yl)propyl)piperazin-1-yl) propylamine,
N,N-diisobutyl-3-[4-(3-(8-methyl-1,3,4,5-tetrahydro-1H-pyrido[4,3-b]indol-2-yl)propyl)piperazin-1-yl]propylamine,
N,N-diisobutyl-3-(4-(3-(8-fluoro-1,3,4,5-tetrahydro-1H-pyrido[4,3-b]indol-2-yl)propyl)piperazin-1-yl)propylamine,
8-Fluoro-2-{3-[4-(3-(pyrrolidin-1-yl)propyl)piperazin-1-yl]propyl}-2,3,4,5-tetrahydro-1H-pyrido[4,3-b]indole,
N,N-diisobutyl-2-(4-(3-(8-m ethoxy-1,3,4,5-tetrahydro-1H-pyrido[4, 3-b]indol-2-yl)propyl)piperazin-1-yl)ethylamine,
N,N-dibenzyl-3-[4-(3-(8-fluoro-1,3,4,5-tetrahydro-1H-pyrido[4,3-b]indol-2-yl)propyl) piperazin-1-yl]propylamine,
3-(4-(3-(8-methoxy-1,3,4, 5-tetrahydro-1H-pyrido[4, 3-b]indol-2-yl)propyl)piperazin-1-yl)propylpiperidine,
N,N-diisobutyl-3-{4-[3-(1-phenyl-1,3,4, 9-tetrahydro-1H-beta-carbolin-2-yl)propyl]piperazin-1-yl}propylamine,
N,N-di isobutyl-3-{4-[3-(6-chloro-1,3,4,9-tetrahydro-1H-beta-carbolin-2-yl)propyl]piperazin-1-yl}propylamine,
N,N-dimethyl-3-(4-(3-(1,3,4,9-tetrahydro-1H-beta-carbolin-2-yl)propyl)piperazin-1-yl)propylamine,
N,N-dimethyl-3-(4-(3-(1-phenyl-1,3,4,9-tetrahydro-1H-beta-carbolin-2-yl)propyl)piperazin-1-yl)propylamine,
N,N-diisobutyl-2-{4-[3-(1,3,4,9-tetrahydro-1H-beta-carbolin-2-yl)propyl]piperazin-1-yl}ethylamine,
1-[3-(piperidin-1-yl)propyl]-4-(3-{1H,2H,3H,4H,9H-pyrido[3,4-b]indol-2-yl}propyl)piperazine,
1-[2-(piperidin-1-yl)ethyl]-4-(3-{1H,2H,3H,4H,9H-pyrido[3,4-b]indol-2-yl}propyl)piperazine, and
N,N-dimethyl-3-(4-(2-(1-phenyl-1, 3,4,9-tetrahydro-1H-beta-carbolin-2-yl)ethyl)piperazin-1-yl)propylamine.

10. A method of non-prophylactic treatment of Alzheimer's Disease comprising administering to a patient in need thereof a pharmaceutically acceptable amount of a compound according to claim 1.

11. A pharmaceutical composition comprising as an active ingredient, a compound according to claim 1 and a pharmaceutically acceptable carrier, diluent, excipient and/or adjuvant.

12. A method for modifying localization or activity of VCP/p97 in a patient in need of non-prophylactic treatment of Alzheimer's Disease, comprising administering to said patient a pharmaceutically acceptable amount of a compound according to claim 1.

* * * * *